United States Patent
Zhang et al.

(10) Patent No.: US 11,963,782 B2
(45) Date of Patent: Apr. 23, 2024

(54) METHOD AND APPARATUS OF ANALYZING THE ECG FREQUENCY PARAMETERS FOR THE DIAGNOSIS OF STEMI DISEASES

(71) Applicant: Hong Kong Centre for Cerebro-Cardiovascular Health Engineering Limited, Hong Kong (HK)

(72) Inventors: Yuanting Zhang, Hong Kong (HK); Ting Xiang, Hong Kong (HK); Nan Ji, Hong Kong (HK)

( * ) Notice: Subject to any disclaimer, the term of this patent is extended or adjusted under 35 U.S.C. 154(b) by 238 days.

(21) Appl. No.: 17/517,716

(22) Filed: Nov. 3, 2021

(65) Prior Publication Data

US 2023/0071185 A1    Mar. 9, 2023

(30) Foreign Application Priority Data

Jul. 27, 2021   (CN) .......................... 202110851179.1

(51) Int. Cl.
   *A61B 5/358*    (2021.01)
   *A61B 5/00*     (2006.01)
   *A61B 5/366*    (2021.01)

(52) U.S. Cl.
   CPC .............. *A61B 5/358* (2021.01); *A61B 5/366* (2021.01); *A61B 5/746* (2013.01)

(58) Field of Classification Search
   None
   See application file for complete search history.

(56) References Cited

U.S. PATENT DOCUMENTS

| 2003/0139678 A1* | 7/2003 | Hoium | A61B 5/339 600/510 |
| 2004/0092834 A1* | 5/2004 | Fang | A61B 5/349 600/509 |
| 2013/0281815 A1* | 10/2013 | Varadan | A61B 5/282 600/388 |

OTHER PUBLICATIONS

Kotriwar et al., Higher order spectral analysis of ECG signals, arXiv preprint arXiv:1809.08451, 2018.
Shaffer et al., "A Critical Review of Ultra-Short-Term Heart Rate Variability Norms Research", Frontiers in Neuroscience, vol. 14, Article 594880, Nov. 19, 2020.
(Continued)

*Primary Examiner* — Kennedy Schaetzle
(74) *Attorney, Agent, or Firm* — Nevin Carmichael Consulting (NCC-IP); Nevin Carmichael

(57) ABSTRACT

This application provides a method and apparatus of analyzing the ECG frequency parameters with applications for the diagnosis of ST-segment elevation myocardial infarction (STEMI) diseases, which relates to the interdisciplinary field of biomedical and science engineering. The method includes obtaining ECG signals from subjects through the designed electrodes; calculating ECG frequency domain parameters of the subjects based on the proposed power spectrum model and getting the analytical validation results after studying and verifying the parameters; generating indicators based on the analytical validation results, which could be potentially used as alternative indicators for STEMI diagnosis; and alerting when the indicators meet preset abnormal conditions. The present embodiment is a powerful tool to diagnose STEMI diseases faster and more effectively and helps patients receive timely assistance and treatment.

21 Claims, 13 Drawing Sheets

(56) References Cited

OTHER PUBLICATIONS

Electrophysiology, Task Force of the European Society of Cardiology the North American Society of Pacing. "Heart rate variability: standards of measurement, physiological interpretation, and clinical use." Circulation, vol. 93, No. 5, pp. 1043-1065, Mar. 1, 1996.

Electrophysiology, Task Force of the European Society of Cardiology and the North American Society of Pacing and Electrophysiology. "Heart rate variability: standards of measurement, physiological interpretation, and clinical use." Guidelines, European Heart Journal (1996) 17, 354-381.

Shaffer et al., "An overview of heart rate variability metrics and norms," Frontiers in public health, vol. 5, pp. 258, 2017.

P. PhysioBank, "Physionet: components of a new research resource for complex physiologic signals," Circulation., vol. 101, No. i23, pp. e215-e220, 2000.

Guyton et al., "Text book of medical physiology 11th ed," VVB Saunders, Philadelphia., 1991, pp. 159-169.

Banez, B. et al., "2017 ESC Guidelines for the management of acute myocardial infarction in patients presenting with ST-segment elevation: The Task Force for the management of acute myocardial infarction in patients presenting with ST-segment elevation of the European Society of Cardiology (ESC)," European Heart Journal (2018) vol. 39, 119-177.

Cox, D.R. et al., "On the superposition of renewal processes," Biometrika., vol. 41, No. 1-2, pp. 91-99, 1954.

Lindner, B., "A brief introduction to some simple stochastic processes," Stochastic Methods in Neuroscience 1., 2009.

Gerstner, W. et al., "Neuronal dynamics: From single neurons to networks and models of cognition," Cambridge University Press., 2014.

Zhang, Y.T. et al., "Distributed random electrical neuromuscular stimulation: Effects of the inter-stimulus interval statistics on the EMG spectrum and frequency parameters," Journal of Rehabilitation Research & Development., vol. 31, No. 4, pp. 303, 1994.

Pan, Z. S. et al., "Motor unit power spectrum and firing rate," Medical and Biological Engineering and Computing., vol. 27, No. 1, pp. 14-18, 1989.

Saul, J.P. et al., "Analysis of long term heart rate variability: methods, 1/f scaling and implications", Computers in cardiology, vol. 14, pp. 419-422, 1988.

Cox, D.R. et al., "The Statistical Analysis of Series of Events", Monographs on Applied Probability and Statistics, 1966, Methuen & Co. Ltd, London.

Weisberg, H.F., "Central Tendency and Variability", Sage, 1992, No. 83, Sage Publications.

\* cited by examiner

METHOD AND APPARATUS OF ANALYZING THE ECG FREQUENCY PARAMETERS FOR THE DIAGNOSIS OF STEMI DISEASES

FIELD OF THE INVENTION

This application relates to the interdisciplinary field of biomedical and science engineering. Specifically, this present invention relates generally to the method and apparatus of analyzing the ECG frequency parameters for the diagnosis of elevation myocardial infarction (STEMI) diseases.

BACKGROUND OF THE INVENTION

The electrocardiogram (ECG) record changes in the electrical activity generated by the heart during each cardiac cycle from the body surface, which has been widely used for diagnosing and monitoring abnormal heart conditions. Heart rate variability (HRV), refers to the fluctuation between the intervals of consecutive heart beats (R-R intervals, RRIs), is a powerful non-invasive quantitative index to assess cardiac dynamics and the state of the Autonomic Nervous System (ANS) which is responsible for regulating cardiac rhythm and cardiac activity. Numerous studies have suggested that decreased HRV is an adverse prognostic factor for various heart diseases, such as MI, chronic heart failure, unstable angina, and other cardiovascular diseases.

Myocardial infarction (MI) is a leading component of the cardiovascular diseases. ST-segment elevation myocardial infarction (STEMI) is a life-threatening, time-sensitive emergency condition which will cause rapid and irreversible damage to cardiac muscle. So STEMI patients must be diagnosed and treated promptly. The abnormal alterations in the cardiac electrical activity are commonly used in the diagnosis and evaluation of STEMI development reflected by the changes of P-QRS-T complexes in the 12-lead ECG, which is still the most easily available and noninvasive procedure for the early diagnosis of MI. In the clinical guideline, ST-segment elevation showed in the P-QRS-T complexes is considered STEMI when the elevation level is higher than the clinical scopes for different groups. Additionally, different ECG leads showing significant ST-segment elevations are indicative of the ischemic area, so that can be used to classify the types of STEMI, such as anterior MI, inferior MI, lateral MI, and posterior MI, and their combinations such as antem-septal MI, antero-laterl MI, and postero-lateral MI. The signs of ST-segment elevation can be seen in leads II, III and avF for inferior MI, leads V3 and V4 for anterior MI, leads V1 to V4 for anterior-septal MI, leads V3 to V6 for antero-lateral MI, and leads I and avL for lateral MI.

ECG signal can be regarded as a composite signal with multiple frequency components produced by various physiological processes in addition to the pacing patterns generated from the S-A node. Therefore, any abnormalities in these physiological processes may lead to variations in the power distribution between constituent frequencies. However, most of studies so far simply either calculate the statistical parameters and/or the spectra of RRIs to study cardiovascular activities, or concentrate only on the P-QRS-T complexes analysis, rather than the analysis of the complete ECG signals with both heart beat intervals and the waveforms, which reflect the wholistic heart neural-physiological-electrical activities. One study by Y. Kotriwar et al., "Higher order spectral analysis of ECG signals," arXiv preprint arXiv:1809.08451, 2018, hypothesized that the subtle changes in the P-QRS-T complexes during each cardiac cycle would affect the changes in power distribution at each frequency component of the whole ECG signal and the results intuitively showed that the spectra of ECG recordings from healthy subjects had less power distribution in the high frequency range, and less variability than that from patients with arrhythmia. Although the method has been examined on the whole ECG signal, it lacked a theoretical basis to explain the variations of ECG power spectrum and failed to quantify some phenomena.

Furthermore, according to the previous reports and guidelines described in F. Shaffer, M. Z. Meehan, and C. L. Zerr, "A Critical Review of Ultra-Short-Term Heart Rate Variability Norms Research," Frontiers in Neuroscience, vol. 14, 2020, Electrophysiology, Task Force of the European Society of Cardiology the North American Society of Pacing. "Heart rate variability: standards of measurement, physiological interpretation, and clinical use." Circulation, vol. 93, no. 5, pp. 1043-1065, 1996, F. Shaffer, and J. P. Ginsberg, "An overview of heart rate variability metrics and norms," Frontiers in public health, vol. 5, pp. 258, 2017, and J. P. Saul, et al., "Analysis of long term heart rate variability: methods, 1/f scaling and implications," Computers in cardiology, vol. 14, pp. 419-422, 1988, the data length for HRV analysis range from less than 1 min to over 24 h with classification of long-term recordings (≥24 h), short-term recordings (2-5 min) and ultra-short-term recordings (<2 min) and the longer recordings are associated with increased HRV. Long-term and short-term analyses reflect different underlying physiological meanings and cannot substitute for each other. Due to the development of wearable sensors in the healthcare devices and the need for monitoring individual's health and well-being status, the interests in ultra-short-term HRV analysis with its applications in wearable devices and mobile health technology are significantly increasing recently. Hence, it is also important to test the frequency parameters obtained from ultra-short-term ECG with the same level of accuracy achieved by the frequency parameters over longer ECG signals, which could be suitable for wearable and mobile health applications in living-free environments.

OBJECTS OF THE INVENTION

An object of the present invention is to provide a method and apparatus for analyzing frequency domain parameters of ECG signals that overcome the above problems or at least partially solve the above problems.

One skilled in the art will derive from the following description other objects of the invention. Therefore, the foregoing statements of object are not exhaustive and serve merely to illustrate some of the many objects of the present invention.

SUMMARY OF THE INVENTION

In a first main aspect, the present invention provides a method of analyzing the ECG frequency parameters, the method comprises:
  obtaining ECG signals from subjects through the designed electrodes; the ECG signals include the ECG signals of ST-elevated leads, the ECG signals of reference leads without ST-segment elevation from STEMI patients or ECG signals of normal leads from healthy subjects;
  calculating the ECG frequency domain parameters of the subjects based on the proposed power spectrum model and getting the analytical validation results after studying and verifying the parameters;

generating indicators based on the analytical validation results, which could be potentially used as alternative indicators for STEMI diagnosis;

and alerting when the indicators meet the preset abnormal conditions.

Preferably, the ECG frequency parameters are studied and verified to get the analytical validation results, including:

the ECG frequency parameters are analyzed and verified by the interactive effect level of HR, HRV and P-QRS-T complexes to obtain the analytical validation results.

Preferably, the subjects include positive sample objects and negative sample objects. The negative sample subjects are patients with ST-segment elevation myocardial infarction and the positive sample are healthy subjects;

the ECG signals of the subjects obtained through designed electrodes include:

obtaining the ECG signals of STEMI patients from the ST-elevated leads in terms of the ischemic area and from reference leads without ST-segment elevation through designed electrodes;

obtaining the ECG signals of healthy subjects from the normal leads which are corresponding to the ST-elevated leads and reference leads of STEMI patients.

Preferably, the proposed ECG frequency parameters are computed from the ECG power density spectra of two leads from the same subject, and at least one of the frequency parameters and frequency shift ratios are obtained by quantifying the frequency distribution phenomena in the PDSs.

Preferably, the ECG frequency parameters include at least one of mean frequency, median frequency, mean frequency shift ratio and median frequency shift ratio.

Preferably, the mean frequency is used to characterize the degree of differentiation between STEMI patients and healthy subjects, and the median frequency is used to characterize the degree of differentiation between STEMI patients and healthy subjects; wherein the mean frequency shift ratio is defined as the quotient of the difference in the frequency parameters between the reference lead and the ST-elevated lead divided by the frequency parameter of the reference lead; and the median frequency shift ratio is defined as the quotient of the difference in the frequency parameters between the reference lead and the ST-elevated lead divided by the frequency parameter of the reference lead.

Preferably, the range of the mean frequency of STEMI patients is approximate 5-9 Hz for ST-elevated leads and approximate 9-14 Hz for reference leads; and the mean frequency of healthy subjects is approximate 7-14 Hz and 8-13 Hz for normal leads which are corresponding to the ST-elevated leads and reference leads.

Preferably, the range of the median frequency of STEMI patients is approximate 3-7 Hz for ST-elevated leads and approximate 7-13 Hz for reference leads; and the range of the median frequency of healthy subjects is approximate 5-12 Hz and 6-12 Hz for normal leads which are corresponding to the ST-elevated leads and reference leads.

Preferably, the mean frequency shift ratio and median frequency shift ratio are approximate 20-50% and 35-65% for STEMI patient while the mean frequency shift ratio and median frequency shift ratio in healthy subjects are below a predetermined threshold and the predetermined threshold comprises 0.

Preferably, the ECG frequency parameters are studied and verified to get the analytical validation results, including:

when the range of the ECG PDSs of subjects are within the first frequency range, the ECG frequency parameters are affected by HR and HRV at a lower level than the first impact level threshold. The ECG frequency parameters are more depended on the P-QRS-T complexes, which reflect the abnormal cardiac condition caused by abnormal cardiac contraction dynamics resulting in the changes of the P-QRS-T complexes;

when the range of the ECG PDSs of subjects are within the second frequency range, the ECG frequency parameters are affected by HR and HRV at a higher level than the second impact level threshold. The ECG frequency parameters can reflect the interactive effects of the HR, HRV and P-QRS-T complexes and the changes of the ECG frequency parameters over different ECG signal lengths are below a predetermined degree of change threshold.

Preferably, the ratio of power in the first two peaks to the power in the first frequency range or second frequency range can be used to characterize the degree of differentiation between STEMI patients and healthy subjects; wherein the ratio in ST-elevated leads is larger than the ratio in reference leads of STEMI patient while the ratios in the two normal leads of healthy subjects are nearly identical.

Preferably, the first frequency range specifically includes 0.05-100 Hz.

Preferably, the second frequency range is smaller than the first frequency range.

Preferably, the designed electrodes include at least one of flexible electrodes, dry electrodes, wet electrodes, and textile electrodes.

Preferably, the alerting includes:
sending local alarm bell to call for help;
ending alarm information to emergency contacts;
sending alarm messages to the emergency center.

In a second main aspect, the invention provides an apparatus of analyzing the ECG frequency parameters, the apparatus comprises:

acquisition module, which is used for obtaining ECG signals from subjects through the designed electrodes; the ECG signals include the ECG signals of ST-elevated leads, the ECG signals of reference leads without ST-segment elevation from STEMI patients or ECG signals of normal leads from healthy subjects;

frequency analysis module, which is used for calculating the ECG frequency domain parameters of the subjects based on the proposed power spectrum model and getting the analytical validation results after studying and verifying the parameters;

generation module, which is used for generating indicators based on the analytical validation results and they could be potentially used as alternative indicators for STEMI diagnosis;

and alarm module, which will alert when the indicators meet the preset abnormal conditions.

Preferably, the frequency analysis module is specifically used for calculating the ECG signals of the subjects based on the proposed power spectrum model to get the ECG frequency domain parameters. The ECG frequency parameters are analyzed and verified by the interactive effect level of HR, HRV and P-QRS-T complexes to obtain the analytical validation results.

Preferably, the subjects include positive sample objects and negative sample objects. The negative sample subjects are patients with ST-segment elevation myocardial infarction and the positive sample are healthy subjects. The acquisition module comprises a first acquisition unit and a second acquisition unit; the first acquisition unit, which is used for obtaining the ECG signals of STEMI patients from the ST-elevated leads in terms of the ischemic area and from reference leads without ST-segment elevation through designed electrodes; the second acquisition unit, which is used for obtaining the ECG signals of healthy subjects from the normal leads and they are corresponding to the ST-elevated leads and reference leads of STEMI patients.

Preferably, the proposed ECG frequency parameters are computed from the ECG power density spectra of two leads from the same subject, and at least one of the frequency parameters and frequency shift ratios are obtained by quantifying the frequency distribution phenomena in the PDSs.

Preferably, the ECG frequency parameters include at least one of mean frequency, median frequency, mean frequency shift ratio and median frequency shift ratio.

Preferably, the mean frequency is used to characterize the degree of differentiation between STEMI patients and healthy subjects, and the median frequency is used to characterize the degree of differentiation between STEMI patients and healthy subjects.

Preferably, the mean frequency shift ratio and/or the median frequency shift ratio can be used for characterizing the degree of differentiation between STEMI patients and healthy subjects; wherein the mean frequency shift ratio is defined as the quotient of the difference in the mean frequency between the reference lead and the ST-elevated lead divided by the mean frequency of the reference lead; and the median frequency shift ratio is defined as the quotient of the difference in the median frequency between the reference lead and the ST-elevated lead divided by the median frequency of the reference lead.

Preferably, the range of the mean frequency of STEMI patients is approximate 5-9 Hz for ST-elevated leads and approximate 9-14 Hz for reference leads; and the mean frequency of healthy subjects is approximate 7-14 Hz and 8-13 Hz for normal leads which are corresponding to the ST-elevated leads and reference leads.

Preferably, the range of the median frequency of STEMI patients is approximate 3-7 Hz for ST-elevated leads and approximate 7-13 Hz for reference leads; and the range of the median frequency of healthy subjects is approximate 5-12 Hz and 6-12 Hz for normal leads which are corresponding to the ST-elevated leads and reference leads.

Preferably, the mean frequency shift ratio and median frequency shift ratio are approximate 20-50% and 35-65% for STEMI patient while the mean frequency shift ratio and median frequency shift ratio in healthy subjects are below a predetermined threshold and the predetermined threshold comprises 0.

Preferably, the frequency analysis module is used specifically for:
when the range of the ECG PDSs of subjects are within the first frequency range, the ECG frequency parameters are affected by HR and HRV at a lower level than the first impact level threshold. The ECG frequency parameters are more depended on the P-QRS-T complexes, which reflect the abnormal cardiac condition caused by abnormal cardiac contraction dynamics resulting in the changes of the P-QRS-T complexes;
when the range of the ECG PDSs of subjects are within the second frequency range, the ECG frequency parameters are affected by HR and HRV at a higher level than the second impact level threshold. The ECG frequency parameters can reflect the interactive effects of the HR, HRV and P-QRS-T complexes and the changes of the ECG frequency parameters over different ECG signal lengths are below a predetermined degree of change threshold.

Preferably, the ratio of power in the first two peaks to the power in the first frequency range or second frequency range can be used to characterize the degree of differentiation between STEMI patients and healthy subjects; wherein the ratio in ST-elevated leads is larger than the ratio in reference leads of STEMI patient while the ratios in the two normal leads of healthy subjects are nearly identical.

Preferably, the first frequency range specifically includes 0.05-100 Hz.

Preferably, the second frequency range is smaller than the first frequency range.

Preferably, the designed electrodes include at least one of flexible electrodes, dry electrodes, wet electrodes, and textile electrodes.

Preferably, the alarm module includes:
sending local alarm bell to call for help;
sending alarm information to emergency contacts;
sending alarm messages to the emergency center.

In a third main aspect, the present invention provides an electronic apparatus, comprising a memory, a processor, and a computer program stored in the memory and running on the processor, wherein the processor executes the program to implement the steps of the analysis method described in the second aspect.

In a fourth main aspect, the present invention provides a computer-readable storage medium, wherein the computer-readable storage medium stores computer instructions that make the computer to execute the steps of the analysis method provided in the second aspect.

In a fifth main aspect, the present invention provides a computer program which includes computer instructions and the computer instructions are stored in a computer-readable storage medium. When the processor of the computer device reads the computer instructions from the computer-readable storage medium, the processor executes the computer instructions, so that the computer device executes the steps for implementing the method provided in the first aspect.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figures, of which.

DESCRIPTION OF PREFERRED EMBODIMENTS

Embodiments of this application are described in detail below, and examples of embodiments are shown in the attached drawings, wherein the same or similar designations from beginning to end indicate the same or similar components or components having the same or similar functions. The embodiments described below by reference to the attached drawings are illustrative and are intended only to explain the present application and not to be construed as a limitation of the present invention.

It will be understood by those of skill in the art that the singular forms "one", "a" and "the" as used herein may also include the plural forms, unless otherwise stated. It should be further understood that the wording "includes" as used in the specification of this application refers to the presence of features, integers, steps, operations, components and/or assemblies, but does not preclude the presence or addition of one or more other features, integers, steps, operations, components, assemblies and/or groups thereof. It should be understood that when an embodiment of this application refers to a component being "connected" or "coupled" to another component, it may be directly connected or coupled to other components, or there may be intermediate components. In addition, "connected" or "coupled" as used herein may include wirelessly connected or wirelessly coupled. The word "and/or" as used herein includes all or any of the units and all combinations of one or more of the associated listed items.

In order to make the purpose, technical solutions and advantages of this application clearer, the following will be described in further detail in conjunction with the accompanying drawings for the implementation of this application.

This invention relates to a method and apparatus of analyzing the ECG frequency parameters, obtaining ECG signals from subjects through the designed electrodes; calculating the ECG frequency domain parameters of subjects based on the proposed ECG power spectrum model and getting the analytical validation results after studying and verifying the parameters; generating indicators based on the analytical validation results, which could be potentially used as alternative indicators for STEMI diagnosis; and alerting when the indicators meet preset abnormal conditions. The present invention is a powerful tool to diagnose STEMI diseases faster and more effectively and helps patients receive timely assistance and treatment.

Figure 1:
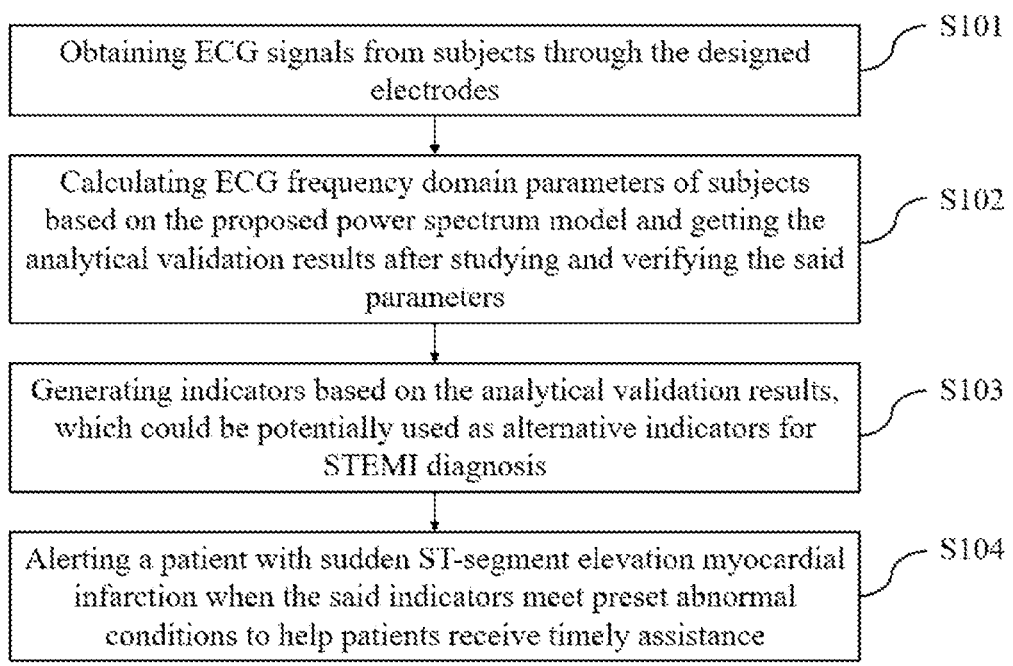
FIG. 1 shows an analysis method of ECG frequency parameters provided in an embodiment of the present invention.

In one embodiment, the present invention provides a method for analyzing the ECG frequency parameters, as shown in FIG. 1, the method comprising:

Step S101, obtaining ECG signals from subjects through the designed electrodes; the said ECG signals include the ECG signals of ST-elevated leads, the ECG signals of reference leads without ST-segment elevation from STEMI patients or ECG signals of normal leads from healthy subjects; the said designed electrodes include at least one of flexible electrodes, dry electrodes, wet electrodes, and textile electrodes.

Electrodes for collecting ECG signals at different parts of the body surface, including electrodes for collecting ECG signals in ST-elevated leads, where the example sample object is a negative sample object; and reference electrodes, which in this apparatus figure are used for collecting ECG signals in reference leads/normal leads without ST-segment elevation.

The sample objects of this application embodiment include positive sample objects and negative sample objects. The said negative sample subjects are patients with ST-segment elevation myocardial infarction and the said positive sample are healthy subjects;

The ECG signal of this application embodiment can be regarded as a composite signal, in addition to the pacing pattern generated from the sinoatrial node (S-A node), there are multiple frequency components generated by various physiological processes, the ECG signal is a very weak physiological low frequency electrical signal, usually the maximum amplitude does not exceed 5 mV, the signal frequency between 0.05 to 100 Hz, the ECG signal is usually through the electrodes mounted on the surface of the human skin to The ECG signal is usually obtained through electrodes installed on the surface of human skin.

Step S102, calculating the ECG frequency domain parameters of the said subjects based on the proposed power spectrum model and getting the analytical validation results after studying and verifying the said parameters.

Specifically, in general, neural electrical impulses at the S-A node of the heart activity do not occur periodically with perfect regularity. Instead, they exhibit random variations around the mean heart rate or mean firing rate. Thus, as the firing of S-A node is affected by the ANS input, the RRIs extracted from the ECG signal exhibit stochastic characteristics.

Figure 2:
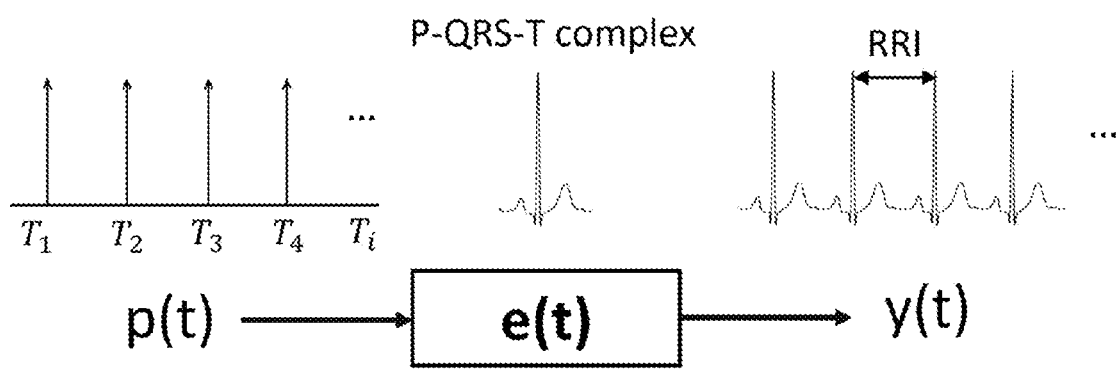
FIG. 2 is a structural block diagram depicting a generation model of ECG signal provided for an embodiment of the present invention.

To simulate the physiological generation of ECG signal, a linear time-invariant system model is proposed as shown in FIG. 2. The input signal p(t) to the system represents the pacing pulse train (PPT) simulating the electrical activities originated at the S-A node, which is a sequence of pulses with discrete random occurrences in continuous time and, as such it is approximated as a renewal random point process with known activation statistics. The impulse response e(t) of the model in FIG. 2 represents the P-QRS-T complex of ECG signal. The output y(t) of the model represents theoretical ECG signal which is determined by the pacing pulse train from S-A node and the P-QRS-T complex reflecting heart contraction dynamics.

The PPT can be approximate to a sequence of impulses described as:

$$p(t) = \Sigma_{i=-\infty}^{\infty} \delta(t - T_i) \quad (1)$$

where a random variable $T_i$ is the reciprocal of the instantaneous pacing/heart rate, $\lambda_i$:

$$\lambda_i = \frac{1}{T_i} \quad (2)$$

The PDS, $\phi_{pp}(f)$ of the model output y(t) representing ECG signal is expressed as:

$$\phi_{yy}(f) = \phi_{pp}(f) |E(f)|^2 \quad (3)$$

where $\phi_{pp}(f)$ is the PDS of the PPT and E(f) is the Fourier transform of e(t). The PDS of ECG signal in equation (3) is the product of $|E(f)|^2$, the energy spectrum of the P-QRS-T complex associated with the cardiac contraction dynamics, and $\phi_{pp}(f)$, the PDS of the pacing pulse train reflecting the S-A node firing patterns. The R-R intervals between successive impulses can be approximated as a sequence of independently distributed random variables with a probability density function (PDF), $f_x(x)$. For a renewal random point process, the PDS of the PPT can be derived based on the previous studies of D. R. Cox, and W. L. Smith, "On the superposition of renewal processes," *Biometrika.*, vol. 41, no. 1-2, pp. 91-99, 1954, D. R. Cox, "The statistical analysis of series of events," *Monographs on Applied Probability and Statistics.*, 1966, B. Lindner, "A brief introduction to some simple stochastic processes," *Stochastic Methods in Neuroscience* 1., 2009 and W. Gerstner, et al., "Neuronal dynamics: From single neurons to networks and models of cognition," Cambridge University Press., 2014.

$$\Phi_{pp}(f) = \lambda \left( 1 + \frac{F_x(f)}{1 - F_x(f)} + \frac{F_x^*(f)}{1 - F_x^*(f)} \right), f \neq 0 \quad (4)$$

where $F_x(f)$ represents the Fourier transform of the PDF $f_x(x)$ of RRIs, $F_x^*(f)$ is the complex conjugate of $F_x(f)$, and $\lambda$ is the mean pacing/heart rate of the ECG signal in pulse per second (pps). This formula form was applied in distributed random electrical neuromuscular stimulation and the spectral analysis of electromagnetic signals in previous studies, Y. T. Zhang, et al., "Distributed random electrical neuromuscular stimulation: Effects of the inter-stimulus interval statistics on the EMG spectrum and frequency parameters," *Journal of Rehabilitation Research & Development.*, vol. 31, no. 4, pp. 303, 1994, and Z. S. Pan, Y. Zhang, and P. A. Parker, "Motor unit power spectrum and firing rate," *Medical and Biological Engineering and Computing.*, vol. 27, no. 1, pp. 14-18, 1989. For a given PDF, the PPT. Both of the foregoing references are incorporated herein by reference. Combining equation (3) and equation (4) yields the PDS of ECG signal, $$\Phi_{yy}(f) = \lambda \left( 1 + \frac{F_x(f)}{1 - F_x(f)} + \frac{F_x^*(f)}{1 - F_x^*(f)} \right) |E(f)|^2, f \neq 0 \quad (5)$$

In this study, RRIs of the ECG signal are assumed to be with a Gaussian PDF, $f_x(x)$. With this assumption, the PDS of ECG signal can be obtained by equation (6), $$\Phi_{yy}(f) = \lambda \frac{\sinh\left[2(\pi f \sigma_x)^2\right]}{\cosh\left[2(\pi f \sigma_x)^2\right] - \cos\left(\frac{2\pi f}{\lambda}\right)} |E(f)|^2, f \neq 0 \quad (6)$$

where $\sigma x$ is the standard deviation of the RRIs, HRV and c is the variation coefficient defined by $c = \sigma x \lambda$ representing the normalized HRV.

The application embodiment obtains the said ECG frequency parameters of the ECG signals for the positive sample objects and the said ECG frequency parameters for the negative sample objects by calculating the ECG signals of the positive sample objects and the ECG signals of the negative sample objects, respectively.

When the ECG frequency parameters are calculated from the PDS in the range of 0.05-100 Hz, the ECG frequency parameters are less influenced by heart rate and heart rate variability and are mainly determined by the P-QRS-T waveform, and the frequency domain parameters are relatively stable over different ECG signal lengths as verified by clinical ECG signal analysis.

The ECG frequency parameters are less affected by HR and HRV compared with the morphology of P-QRS-T complexes when calculated from 0.05 Hz to 100 Hz and through the said clinical analysis, the said parameters are relatively stable over the tested entire data lengths. When the said parameters are calculated from 0.05 Hz-20 Hz, which can reflect the interactive effects of heart rhythm statistics and P-QRS-T complexes. For other abnormal cardiac conditions mainly caused by abnormal heart rhythm statistics such as arrhythmia, tachycardia, bradycardia, the said parameters calculated from the said range can not only reflect the effects of heart rhythm statistics but the P-QRS-T complexes associated with the cardiac contraction dynamics as well. It means that different calculation ranges of the said parameters can reflect different dominated effects of abnormal cardiac condition.

(1) when the calculation range of the said ECG PDSs of subjects is relatively wide, the said ECG frequency parameters are less affected by HR and HRV but more depended on the P-QRS-T complexes, which reflect the abnormal cardiac condition caused by abnormal cardiac contraction dynamics resulting in the changes of the P-QRS-T complexes;

(2) when the calculation range of the said ECG PDSs of subjects is relatively small, the said ECG frequency parameters can reflect the interactive effects of the HR, HRV and P-QRS-T complexes which can not only reflect the abnormal heart contraction, but also the lesions that occur with abnormal electrical impulse conduction.

The ECG PDSs of the STEMI patients of this application embodiment are calculated from the ST-elevated leads in terms of the ischemic area and the reference leads without ST-segment elevation. The ECG PDSs of the healthy subjects are calculated from the normal leads which are corresponding to the said ST-elevated leads and the reference leads of STEMI patient.

In order to verify the above-described theoretical model, This application embodiment performs the PDS analysis of clinical ECG recordings of STEMI patients and healthy subjects from an existing database. The raw ECG datasets analyzed in the invention are obtained from PTB Diagnostic Database (PTBDB) and European ST-T Database (EDB) in 'Physionet', which are available on P. PhysioBank, "Physionet: components of a new research resource for complex physiologic signals," *Circulation.*, vol. 101, no. i23, pp. e215-e220, 2000. Each subject in EDB was diagnosed or suspected as myocardial ischemia, the ECG recordings of which are two hours in duration and contain two leads. 98 ECG datasets of 60 s from 49 STEMI patients and 210 ECG datasets of 60 s from 42 healthy subjects in PTBDB were included for PDS analysis. 33 ECG datasets with ST-segment elevation of 60 mins from 33 MI patients in EDB were selected to calculate the MNF and MDF over different segment lengths ranging from the ultra-short-term of 10 s to 60 mins.

In order to evaluate and quantify the power distributions showed in the PDSs of ECG signals with different HRs, HRVs and P-QRS-T complexes, MNF and MDF of PDSs are calculated from 0.05 Hz to 100 Hz, which contained most of the useful information about the ECG signals in frequency domain. The leads without ST-segment elevation in STEMI patients are regarded as reference leads. Another parameter is the frequency shift ratio of MNF or MDF, which is defined as the quotient of the difference in the frequency parameters between the reference lead and the ST-elevated lead divided by the frequency parameter of the reference lead.

Figure 3:
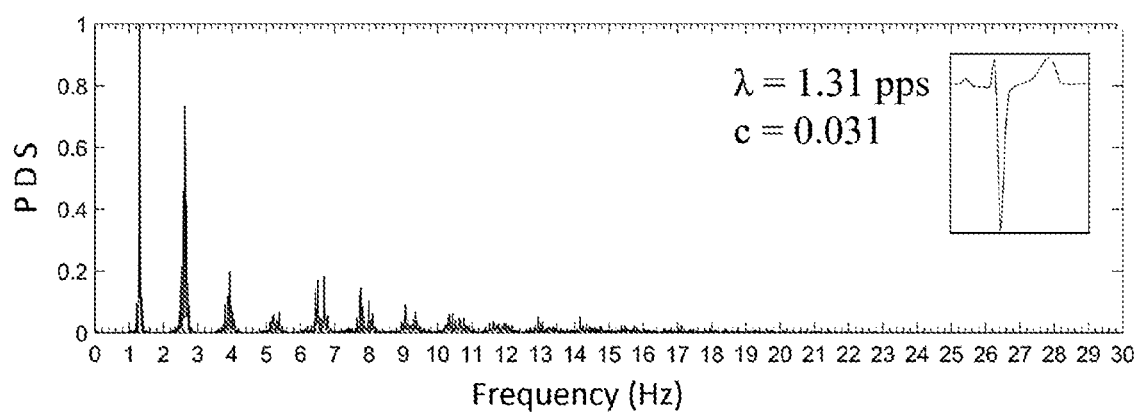
FIG. 3 is a graph describing the PDS of a typical healthy ECG signal for an embodiment of the present invention.

The features of theoretical PDS of ECG signal with the Gaussian distributed RRIs, supported by experimental results of clinical ECG signals, are summarized as follows:

1. The ECG PDS has normally peaks at harmonics of the mean pacing/heart rate for the RRIs with Gaussian PDF $f_x(x)$. This observation can be deduced from equation (6). The spectral peaks of the ECG PDS are generated by the cosine component in equation (6) with $f=k\lambda$, (k=1, 2, 3 ... ). Besides, the frequency corresponding to the first peak is equal to the $\lambda$. This observation from the mathematical model can be seen in the experimental PDS of ECG signal as illustrated in FIG. 3 showing the PDS from a normal subject with values of $\lambda=1.31$ pps and c=0.031.
2. The magnitudes and the numbers of the peaks in the ECG PDS rely on the normalized HRV, c. This phenomenon can be explained by substituting $f=k\lambda$ into equation (6) for the Gaussian intervals. Equation (6) becomes, $$\Phi_{yy}(f,c) = \lambda \frac{\sinh\left[2(\pi kc)^2\right]}{\cosh\left[2(\pi kc)^2\right]-1}|E(f)|^2, f \neq 0 \tag{7}$$

The magnitudes of most peaks in the ECG PDS become large when the normalized HRV, c is small. This trend can be seen in the experimental result showed in FIG. 4, where the magnitudes of most peaks are higher with a smaller value of c in comparison with that in FIG. 3. The number of the peaks in the PDS is also influenced by the value of c, which can be verified by equation (7) and illustrated in FIGS. 3 and 4.

3. The PDS of ECG signal depends not only on the c as seen above but also on the spectrum of P-QRS-T complex, E(f) as expected. Substituting equation (6) for $\phi_{pp}(f)$ with a Gaussian distributed RRIs, let $\sigma_x=\sigma$, the PDS in equation (6) can be written as, $$\Phi_{yy}(f) = \lambda \frac{\sinh\left[2(\pi f\sigma)^2\right]}{\cosh\left[2(\pi f\sigma)^2 - 1\right]}|E(f)|^2, f \neq 0 \tag{8}$$

Figure 4:
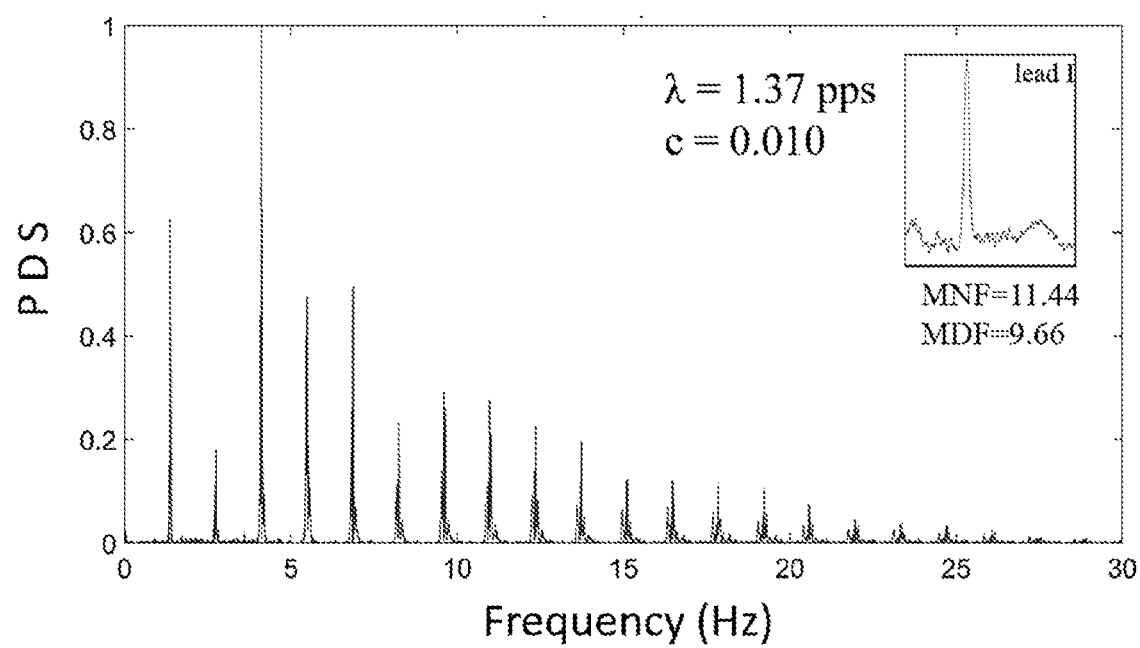
FIG. 4 is a graph describing the PDS of lead I (standard limb lead) ECG signal from a STEMI patient for an embodiment of the present invention.
Figure 5:
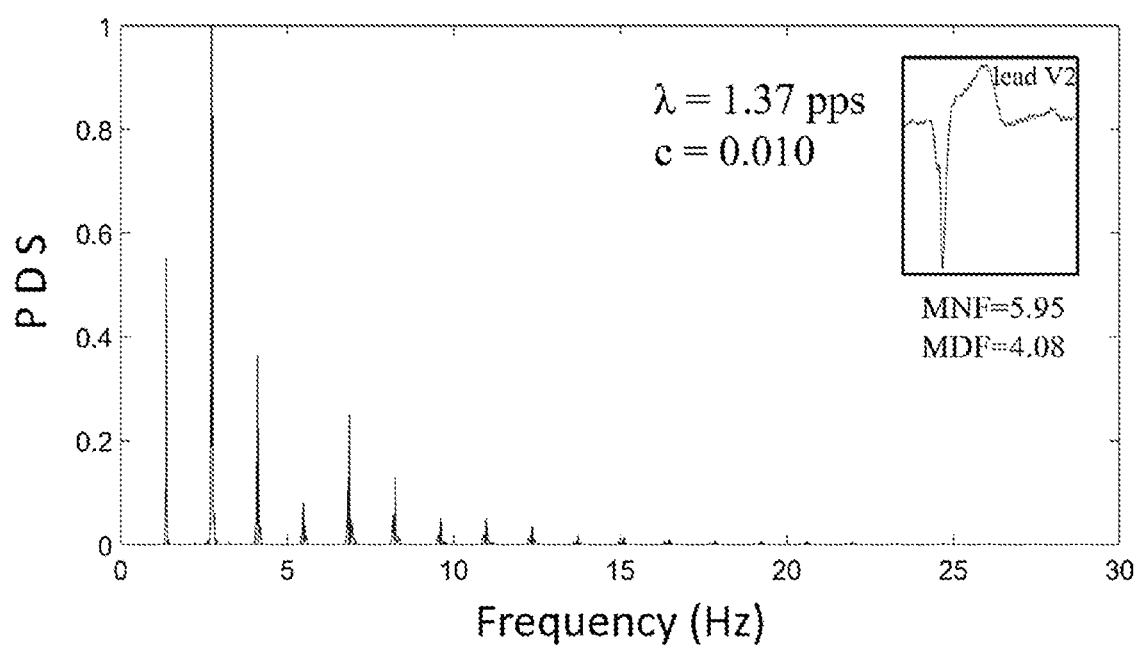
FIG. 5 plots the PDS of lead V2 (chest lead) ECG signal from a STEMI patient for an embodiment of the present invention, the STEMI patient in FIG. 5 is the same patient as FIG. 4.

Equation (8) illustrates that the PDS envelope of ECG signal is controlled by the spectrum, E(f) while the detailed changes in the PDS are associated with the RRIs statistics under various conditions. In FIG. 4 and FIG. 5, the ECG PDS of lead I (standard limb lead) is compared with the lead V2 (chest lead) showing ST-segment elevation in the same STEMI person, which have different P-QRS-T complexes but the same values for $\lambda$ and c. It can be seen that the amplitudes of spectral peaks distributed in low frequency range of lead V2 are higher than those of lead I as reference lead in the same MI patients. For the lead V2, the main power distribution generally shifts towards the low frequency range below 5-8 Hz while for the lead I. the power range extends to 8-15 Hz with higher variability in the spectrum. The spectral differences between the lead I and lead V2 are resulted from the different P-QRS-T complexes in the time domain. In FIG. 5, the MNF and MDF of the PDSs are lower in lead V2 (MNF=5.95 Hz, MDF=4.08 Hz) than in lead I (MNF=11.44 Hz, MDF=9.66 Hz), indicating MNF and MDF maybe possible indicators to diagnose STEMI through evaluating and quantifying the power shift in the PDSs caused by the changes of P-QRS-T complexes in different leads.

It can be seen from Tables I that all the values of MNF and MDF were lower in ST-elevated leads compared with the reference leads for STEMI patients. For anterior MI (n=12), MNF and MDF in lead V3 were statistically significant lower than in lead I (6.88±1.00 Hz vs 11.34±2.01 Hz, p<0.0001; 4.77±1.18 Hz vs 10.16±2.29 Hz, p<0.0001). The shift ratios of MNF and MDF in anterior MI were 38.27±11.64% and 51.39±12.94%.

TABLE I

Mean Frequency and Median Frequency of Anterior MI

| Anterior MI | Mean frequency | | | Median frequency | | |
|---|---|---|---|---|---|---|
| (n = 12) | Lead 1 (Hz) | Lead V3 (Hz) | Shift ratio | Lead 1 (Hz) | Lead V3 (Hz) | Shift ratio |
| 1 | 10.39 | 6.15 | 40.81% | 9.22 | 4.02 | 56.40% |
| 2 | 15.23 | 5.82 | 61.79% | 14.13 | 3.40 | 75.94% |
| 3 | 9.00 | 6.82 | 24.22% | 7.58 | 4.69 | 38.13% |
| 4 | 13.16 | 6.03 | 54.18% | 11.93 | 3.92 | 67.14% |
| 5 | 14.22 | 8.08 | 43.18% | 14.15 | 7.11 | 49.75% |
| 6 | 8.54 | 6.71 | 27.75% | 7.22 | 5.4 | 25.21% |
| 7 | 9.97 | 5.55 | 44.33% | 9.36 | 3.93 | 58.01% |
| 8 | 10.45 | 5.76 | 44.88% | 8.29 | 3.68 | 55.61% |
| 9 | 11.00 | 8.16 | 25.82% | 9.35 | 4.70 | 49.73% |
| 10 | 10.63 | 7.17 | 32.55% | 9.58 | 4.15 | 56.68% |
| 11 | 13.11 | 8.42 | 35.77% | 12.38 | 7.08 | 42.81% |
| 12 | 10.40 | 7.91 | 23.94% | 8.73 | 5.13 | 41.24% |
| Mean ± SD | 11.34 ± 2.01 | 6.88 ± 1.00 | 38.27 ± 11.64% | 10.16 ± 2.29 | 4.77 ± 1.18 | 51.39 ± 12.94% |
| p-value | <0.0001 | | | <0.0001 | | |

Similarly, as shown in Table 11, MNF and MDF in ST-elevated leads were statistically significant lower than in reference leads for antero-septal MI (6.64±1.12 Hz vs 10.67±1.94 Hz, $p<0.0001$; 4.70±1.05 Hz vs 9.14±2.02 Hz, $p<0.0001$) and the shift ratios of MNF and MDF were 37.86±10.83% and 47.41±10.80% in antero-septal MI.

TABLE II

Mean Frequency and Median Frequency of Antero-septal MI

| Antero-septal MI | Mean frequency | | | Median frequency | | |
|---|---|---|---|---|---|---|
| (n = 21) | Lead 1 (Hz) | Lead V2 (Hz) | Shift ratio | Lead 1 (Hz) | Lead V2 (Hz) | Shift ratio |
| 1 | 11.44 | 5.95 | 47.99% | 9.66 | 4.08 | 57.76% |
| 2 | 12.59 | 8.86 | 29.63% | 10.04 | 7.14 | 28.88% |
| 3 | 13.25 | 5.78 | 56.38% | 11.87 | 4.38 | 63.10% |
| 4 | 10.07 | 5.91 | 47.67% | 8.79 | 4.82 | 45.16% |
| 5 | 11.15 | 6.09 | 45.38% | 8.33 | 4.86 | 41.66% |
| 6 | 14.47 | 6.42 | 55.63% | 13.29 | 4.95 | 62.75% |
| 7 | 8.96 | 5.40 | 39.73% | 6.66 | 3.97 | 40.39% |
| 8 | 10.89 | 6.59 | 39.49% | 9.91 | 4.11 | 58.53% |
| 9 | 11.76 | 7.63 | 35.12% | 9.92 | 6.17 | 37.80% |
| 10 | 11.88 | 9.07 | 23.65% | 10.40 | 7.13 | 31.44% |
| 11 | 10.47 | 6.93 | 33.81% | 9.44 | 4.80 | 49.15% |
| 12 | 9.36 | 7.40 | 20.94% | 8.59 | 5.32 | 38.07% |
| 13 | 6.26 | 4.25 | 32.11% | 5.48 | 2.78 | 49.27% |
| 14 | 8.11 | 5.94 | 26.76% | 6.73 | 4.10 | 39.08% |
| 15 | 11.18 | 7.33 | 34.44% | 8.61 | 4.65 | 45.99% |
| 16 | 10.20 | 6.02 | 40.98% | 8.60 | 4.25 | 50.58% |
| 17 | 8.70 | 6.62 | 23.91% | 7.39 | 3.58 | 51.56% |
| 18 | 13.76 | 5.38 | 60.90% | 13.83 | 3.88 | 71.95% |
| 19 | 8.80 | 5.93 | 32.61% | 7.41 | 3.72 | 49.80% |
| 20 | 9.38 | 6.08 | 35.18% | 7.88 | 5.13 | 34.90% |
| 21 | 11.42 | 7.68 | 32.75% | 9.18 | 4.79 | 47.82% |
| Mean+SD | 10.67 ± 1.94 | 6.64 ± 1.12 | 37.86 ± 10.83% | 9.14 ± 2.02 | 4.70 ± 1.05 | 47.41 ± 10.80% |
| p-value | <0.0001 | | | <0.0001 | | |

As shown in Table. 3, MNF and MDF in ST-elevated leads were statistically significant lower than in reference leads for inferior MI (7.83±1.54 Hz vs 12.48±1.96 Hz, $p<0.0001$; 5.42±1.45 Hz vs 11.38±2.26 Hz, $p<0.0001$) and the shift ratios of MNF and MDF of inferior MI were 36.06±14.93% and 50.72±15.56%.

TABLE III

Mean Frequency and Median Frequency of Inferior MI

| Inferior MI | Mean frequency | | | Median frequency | | |
|---|---|---|---|---|---|---|
| (n=16) | Lead V5 (Hz) | Lead III (Hz) | Shift ratio | Lead V5 (Hz) | Lead HI (Hz) | Shift ratio |
| 1 | 15.82 | 10.23 | 35.34% | 14.93 | 9.03 | 39.52% |
| 2 | 11.14 | 7.11 | 36.18% | 10.58 | 4.41 | 58.32% |
| 3 | 13.31 | 9.51 | 28.55% | 11.58 | 6.28 | 45.77% |
| 4 | 10.26 | 8.86 | 13.65% | 8.69 | 6.17 | 29.00% |

TABLE III-continued

Mean Frequency and Median Frequency of Inferior MI

| Inferior MI | Mean frequency | | | Median frequency | | |
|---|---|---|---|---|---|---|
| (n=16) | Lead V5 (Hz) | Lead III (Hz) | Shift ratio | Lead V5 (Hz) | Lead III (Hz) | Shift ratio |
| 5 | 13.67 | 5.88 | 56.99% | 12.58 | 3.81 | 69.71% |
| 6 | 13.14 | 6.94 | 47.18% | 12.60 | 4.73 | 62.46% |
| 7 | 11.55 | 6.42 | 44.42% | 10.54 | 4.88 | 53.70% |
| 8 | 11.75 | 8.92 | 24.09% | 10.68 | 4.93 | 53.84% |
| 9 | 11.58 | 6.43 | 44.47% | 9.97 | 3.85 | 61.38% |
| 10 | 10.84 | 6.70 | 38.19% | 9.36 | 4.05 | 56.73% |
| 11 | 14.26 | 5.47 | 61.64% | 13.50 | 4.07 | 69.85% |
| 12 | 10.05 | 9.12 | 9.25% | 8.53 | 6.88 | 19.34% |
| 13 | 11.87 | 6.46 | 45.58% | 10.70 | 4.48 | 58.13% |
| 14 | 11.09 | 7.89 | 28.85% | 9.53 | 6.69 | 29.80% |
| 15 | 17.46 | 8.99 | 48.51% | 17.24 | 5.10 | 70.42% |
| 16 | 11.99 | 10.31 | 14.01% | 11.03 | 7.33 | 33.54% |
| Mean ± SD | 12.48 ± 1.96 | 7.83 ± 1.54 | 36.06 ± 14.93% | 11.38 ± 2.26 | 5.42 ± 1.45 | 50.72 ± 15.56% |
| p-value | <0.0001 | | | <0.0001 | | |

After the comparison in the 3 tables, the shift ratios of MNF and MDF were 38.27±11.64% and 51.39±12.94% in anterior MI, 37.86±10.83% and 47.41±10.80% in anteroseptal MI, 36.06±14.93% and 50.72±15.56% in inferior MI.

Figure 6:
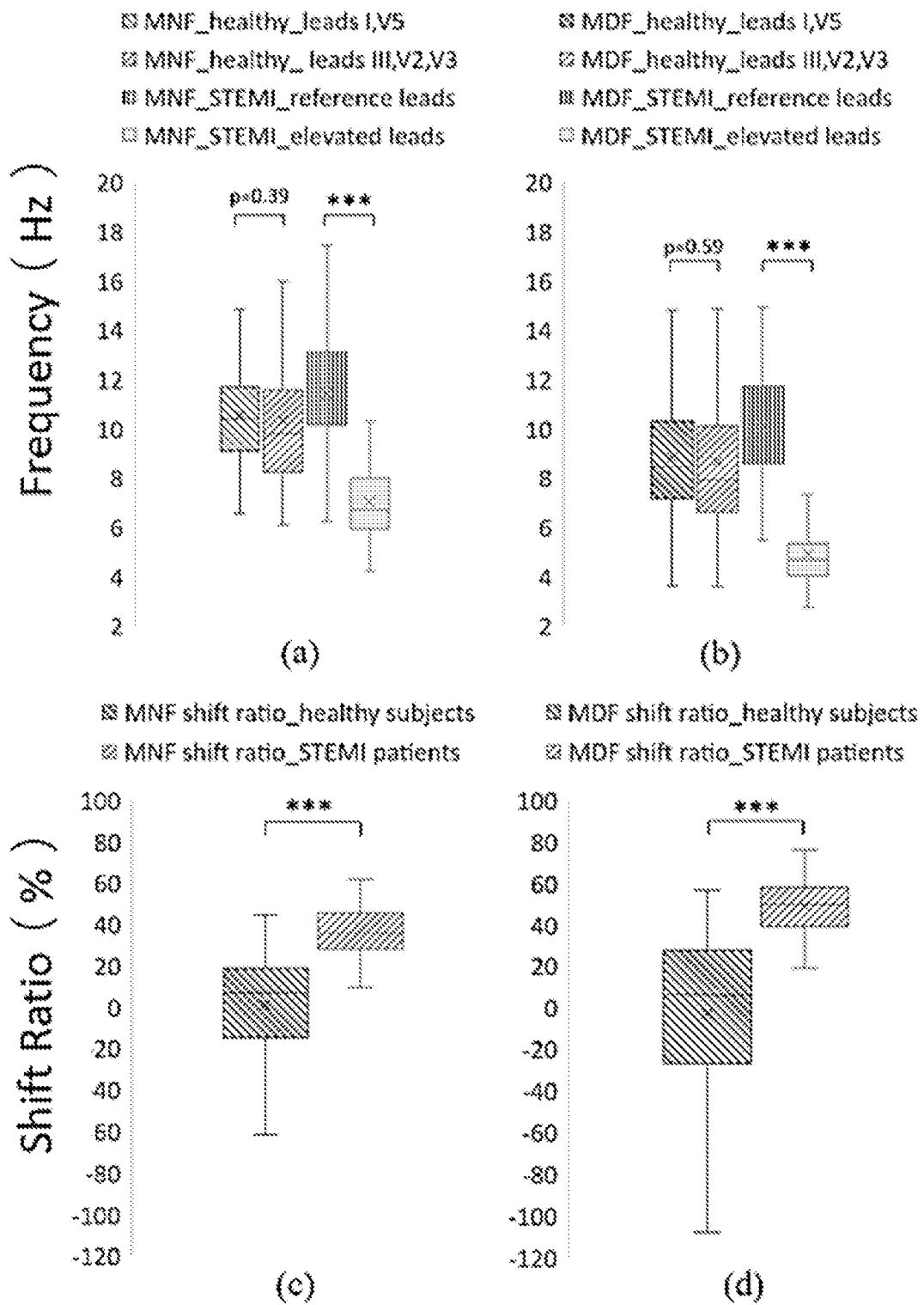
FIG. 6 is the boxplots of (a) MNF and (b) MDF among leads I, V5 (corresponding to reference leads of STEMI patients), leads III, V2, V3 (corresponding to elevated leads of STEMI patients) in healthy subjects, reference leads and ST-elevated leads of three types of STEMI; (c) MNF shift ratio and (d) MDF shift ratio of healthy subjects and STEMI patients. The boxes display median, 25th, 75th percentiles (solid line), mean (cross), and the whiskers indicate the range of values excluding outliers. "***" indicates statistical significance at $p<0.0001$.

In addition to the statistical analysis on MNF, MDF and their shift ratios of 3 types of STEMI separately, data from these 3 types of STEMI were combined for subsequent analyses with comparison of healthy subjects. The box plots in FIG. 6 showed the full distribution of the frequency parameters and their shift ratios between healthy subjects and 3 types of STEMI patients in our study. It can be seen in FIG. 6(a), on average, the MNF of leads I, V5 (10.55 Hz) and leads III, V2, V3 (10.34 Hz) of healthy subjects and reference leads (11.43 Hz) of STEMI patients were distributed in higher ranges compared with ST-elevated leads (7.04 Hz). Similar results were noted for MDF as shown in FIG. 6(b), that the MDF distributed within a lower range in ST-elevated leads (4.95 Hz) compared with normal leads (8.83 Hz, 8.68 Hz) from healthy subjects and reference leads of STEMI patients (10.12 Hz). There were no significant differences between the MNF (p=0.39) and MDF (p=0.59) of leads I, V5 (corresponding to reference leads) and leads III, V2, V3 (corresponding to ST-elevated leads) of healthy subjects while the MNF and MDF (p<0.0001) of ST-elevated leads were significantly lower than in reference leads by the paired Student's t-test. As plotted in FIGS. 6(c) and 6(d), the MNF shift ratios and the MDF shift ratios of STEMI patients were 37.37% and 49.47% respectively, showing distinct and consistent frequency shift towards the lower frequency range in the ST-elevated leads compared with those reference leads, while the shift ratios of MNF and MDF in healthy subjects presented lower shift ratios and even negative values. Besides, the statistical results showed that there were significant differences between the MNF, MDF based shift ratios of healthy subjects and those of STMEI patients (p<0.0001). Thus, all the results strongly suggested that the feasibility of using MNF and MDF and their shift ratios calculated from the PDS of ultra-short-term ECG for the preliminary screening of STEMI and distinguish healthy people from STEMI patients.

The proposed power spectrum model in this application embodiment takes the P-QRS-T complexes as the impulse response of a linear time-invariant system and a pacing pulse train (PPT) with random R-R intervals (RRIs) mimicking the S-A node fittings as the input to the system. Based on the model, the equations showing the interactive effects of heart rate (HR), its variability and P-QRS-T complexes on the PDS of ECG signal are derived. Additionally, the PDS analysis of clinical ECG recordings of healthy subjects and STEMI patients from existing databases is carried out to verify the theoretical results and to study potential indicators for the diagnosis of STEMI diseases based on the statistical analysis.

Step S103, generating indicators based on the said analytical validation results, which could be potentially used as alternative indicators for STEMI diagnosis.

The indicator information of this application embodiment is used for medical diagnosis of ST-segment elevation myocardial infarction.

The implementation of this application is carried out by computer simulation to verify the reliability of MNF, MDF and their shift ratios for quantifying frequency shift phenomena of the ECG PDSs. The interactive effects of firing statistics and P-QRS-T complex on the PDSs and frequency parameters were analyzed using simulated ECGs with various values of HRs, HRVs, and a same P-QRS-T complex extracted from a STEMI patient. The ECG signals are simulated based on a linear time-invariant filtering system model and are implemented in Matlab. The simulated ECG are generated by convoluting the pacing pulse train described as a random point process with Gaussian distributed PPTs assigned with practical values within the ranges studied in clinical ECG signals with P-QRS-T complex, which is randomly extracted from a cycle of the clinical ECG recordings in terms of the typical morphology described in A. C. Guyton, and J. E. Hall, "Text book of medical physiology 8th ed," VVB Saunders, Philadelphia., 1991, pp. 159-169 and B. Ibanez et al., "2017 ESC Guidelines for the management of acute myocardial infarction in patients presenting with ST-segment elevation: The Task Force for the management of acute myocardial infarction in patients presenting with ST-segment elevation of the European Society of Cardiology (ESC)," European Heart Journal., vol. 76, no. 2, pp. 229-313, 2018 by eyeballing.

The results of MNF and MDF of PDSs of clinical ECGs and simulation ECGs of 60 s and their normalized differences in three cases randomly selected from three types of STEMI in PTBDB are shown in Table IV.

The consistency between the frequency parameters of simulated ECGs and clinical ECGs is evaluated in terms of the normalized difference. It is observed in Table IV that the normalized differences between clinical and simulation ECG in all three cases are within 9%.

Figure 9:
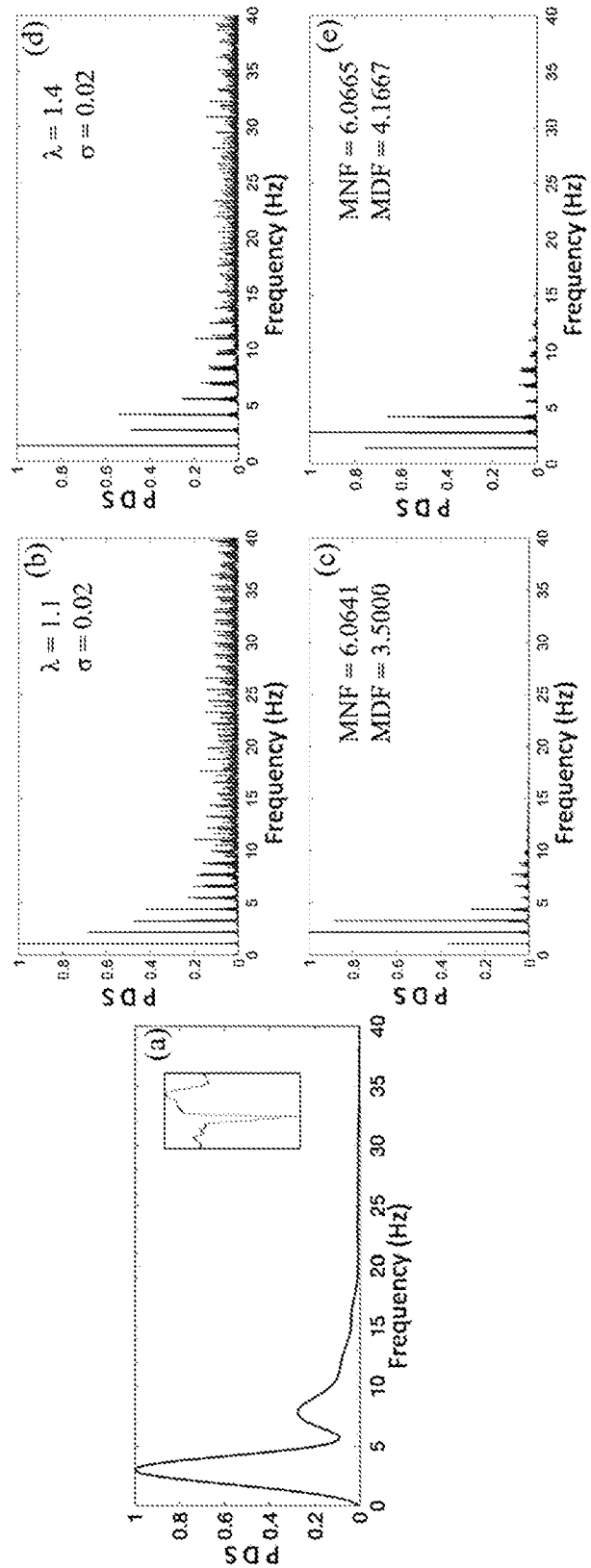
FIG. 9 shows the effects of changes in λ on the PDS of the ECG signal for σ=0.02: (a) power spectrum of the P-QSR-T complex extracted from a STEMI patient; (b)(d) PDSs of simulated PPT with λ=1.1 and =1.4; and (c)(e) PDSs of the ECG signals from multiplying (a) by (b) and multiplying (a) by (d), respectively.

It was noted from FIG. 9 and corresponding equation (3) that with the same power spectrum of P-QRS-T complex,

TABLE IV

Frequency parameters of PDS of ECG signal from patients with different type of STEMI

| Type | ECG lead | Mean Frequency (Hz) | | | Median Frequency (Hz) | | |
|---|---|---|---|---|---|---|---|
| | | Clinical Data | Simulation | Normalized Difference | Clinical Data | Simulation | Normalized Dif |
| Antero-septal MI | Lead I | 8.96 | 8.8136 | 1.63% | 6.66 | 6.5833 | 1.15% |
| | Lead V2 | 5.40 | 5.4418 | 0.77% | 3.97 | 3.9583 | 0.29% |
| | Shift Ratio | 39.73% | 38.26% | | 40.39% | 39.87% | |
| Anterior MI | Lead I | 10.39 | 10.8007 | 3.95% | 9.22 | 9.4833 | 2.86% |
| | Lead V3 | 6.15 | 6.148 | 0.03% | 4.02 | 3.9833 | 0.91% |
| | Shift Ratio | 40.81% | 43.08% | | 56.40% | 58.00% | |
| Inferior MI | Lead V5 | 10.84 | 10.9533 | 1.05% | 9.36 | 9.4 | 0.43% |
| | Lead III | 6.70 | 7.2659 | 8.45% | 4.05 | 4.0833 | 0.82% |
| | Shift Ratio | 38.19% | 33.66% | | 56.73% | 56.56% | |

Figure 7:
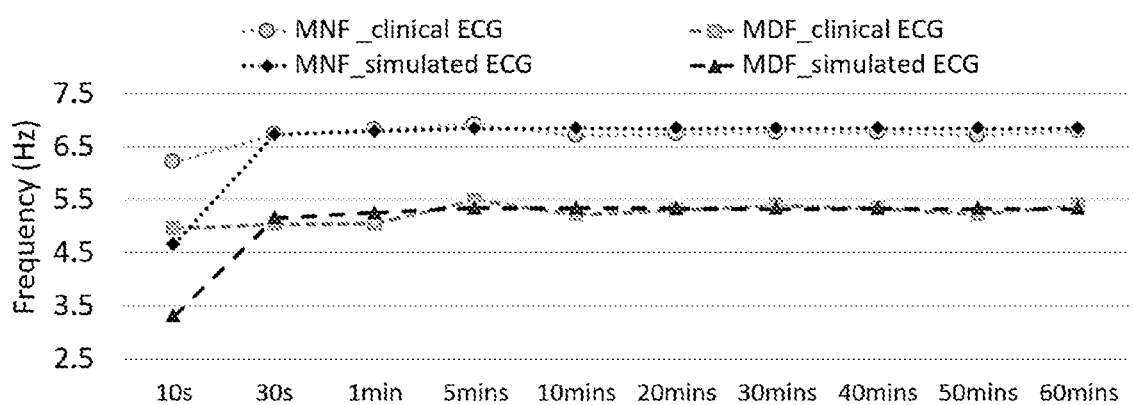
FIG. 7 shows the comparison of frequency parameters between PDSs of clinical ECG and simulated ECG over different segment lengths for an embodiment of the present invention.

FIG. 7 shows the frequency parameters calculated from the PDSs of a longer clinical ECG with ST-segment elevation randomly selected from EBD and the corresponding simulated STEMI ECG over different segment lengths ranging from 10 s to 60 mins. The normalized differences of MNF and MDF between clinical and simulated ECG calculated from different segments were within 5% when the lengths of ECG signals were longer than 30 s. The small errors confirmed that the proposed approach of using the extracted P-QRS-T complex as the response approximation of a linear time-invariant filtering system worked well in simulating clinical ECG in terms of its PDS. Additionally, the frequency parameters calculated from PDSs of simulated ECGs were in close agreement with those calculated from PDSs of clinical ECGs.

All the results of simulation and clinical studies strongly suggest that the MNF and MDF with the minimal effects of HR and HRV but instead they are dominated by morphological changes in P-QSR-T complexes. The proposed frequency parameters obtained from ultra-short-term ECG of 60 s (or even shorter to 30 s) can differentiate the STEMI patients from healthy subjects with the same level of accuracy achieved by the frequency parameters over longer ECG signals of 60 mins, which provided the possibility of using the ultra-short-term frequency parameters in wearable devices and its applications in wearable based-mHealth to qualitatively measure the frequency shift phenomena for the diagnosis of STEMI diseases.

Figure 8:
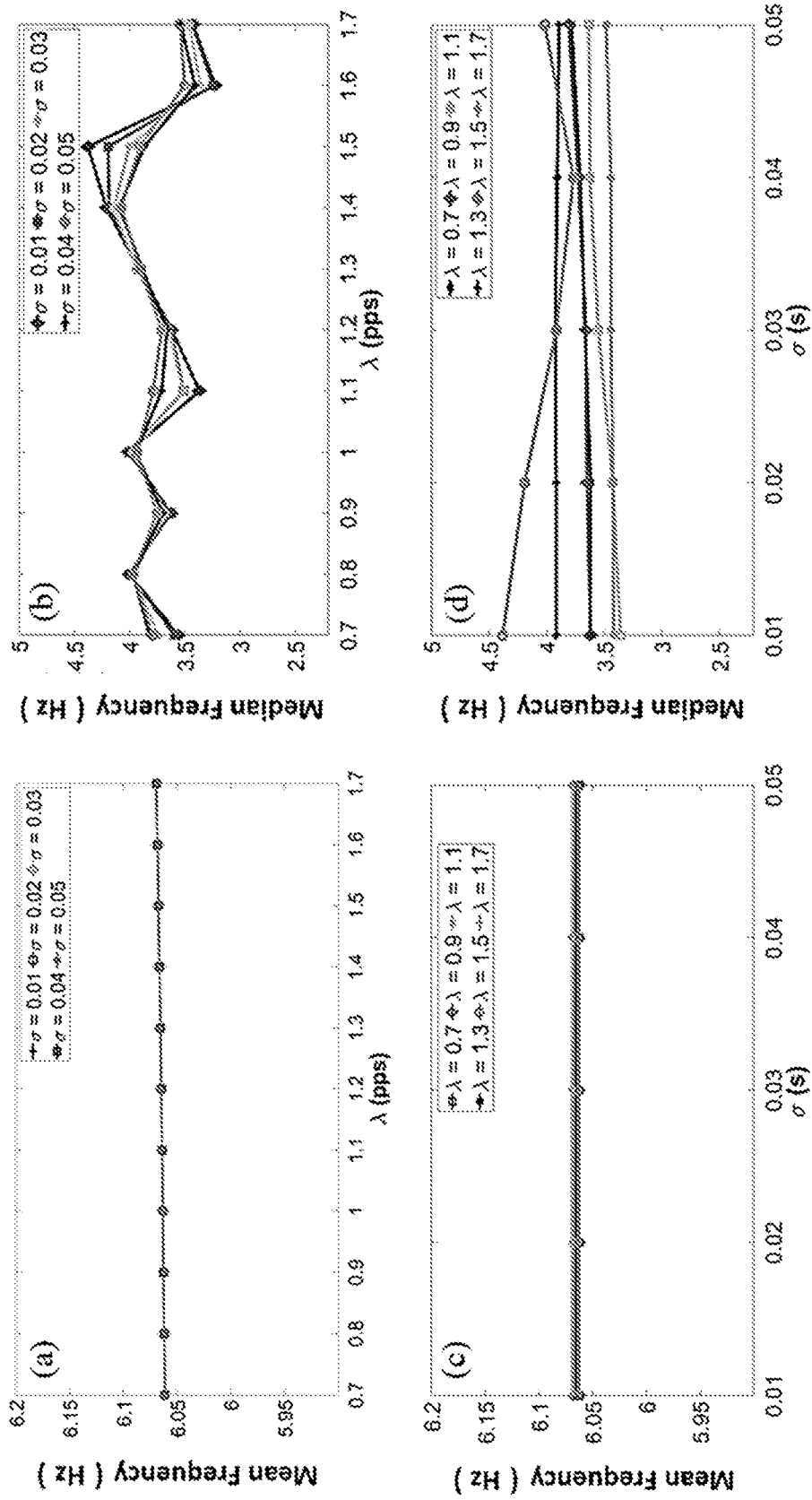
FIG. 8 shows (a) MNF and (b) MDF of the PDS as a function of λ for different values of a. (c) MNF and (d) MDF of the PDS as a function of a for different values of λ.

FIGS. 8(a) and 8(c) plot the trend of MNF as the function of PPT statistics. It can be seen in FIG. 8(a) that the MNF increased slightly as the HR, λ increased from 0.7 to 1.7 Hz for the given different values of HRV, σ. FIG. 8(c) showed that for different values of λ, the MNF remained nearly constant in the studied range of σ. According to the definition of mean frequency and the results of equation (7), the larger λ lead the peaks of the PDS associated with HR to move towards higher frequency range, so accordingly the power distribution shifted to higher frequency range, which resulted in a higher MNF. Based on the observation that the magnitudes and the numbers of peaks in PDS depend on HRV, the small changes in a contributed little effects on the PDS and thus, MNF basically remained steady with increasing values of a.

FIGS. 8(b) and 8(d) show the apparently nonlinear relations between the MDF and PPT statistics. According to equation (3), the PDS of ECG signal was the multiplication of the PDS of the PPT, $\phi_{pp}(f)$ and the spectrum of P-QRS-T complex, $|E(f)|^2$.

the PDSs of PPT with different statistics leads to different distributions of the main peaks in ECG PDSs. Furthermore, MDF is theoretically governed by the central tendency based on H. Weisberg, and H. F. Weisberg, Central tendency and variability, Sage, 1992, no. 83, meaning that MDF is susceptible to the varying magnitudes and locations of the main peaks in PDSs, which explains why the MDF moved up and down and out-of-order as the function of PPT statistics.

Mean absolute percentage error (MAPE) between the frequency parameters calculated from the PDS of simulated ECG of different lengths and those of the theoretical PDS were used to evaluate the influence of the signal segment length on the accuracy of MNF and MDF. The MAPE of the MNF and MDF between the PDS of simulated ECG and theoretical PDS for different values of a within physiological range calculated on each segment of 10 s, 30 s, 1 min, 5 mins, 10 mins, 20 mins, 30 mins, 40 mins, 50 mins and 60 mins. It can be seen that with increasing in the length of the ECG recording, the MAPEs of MNF, MDF and their ratios deceased significantly for all the values of a and trended to approach zero when the length of the data segment was longer than 5 mins.

Figure 10:
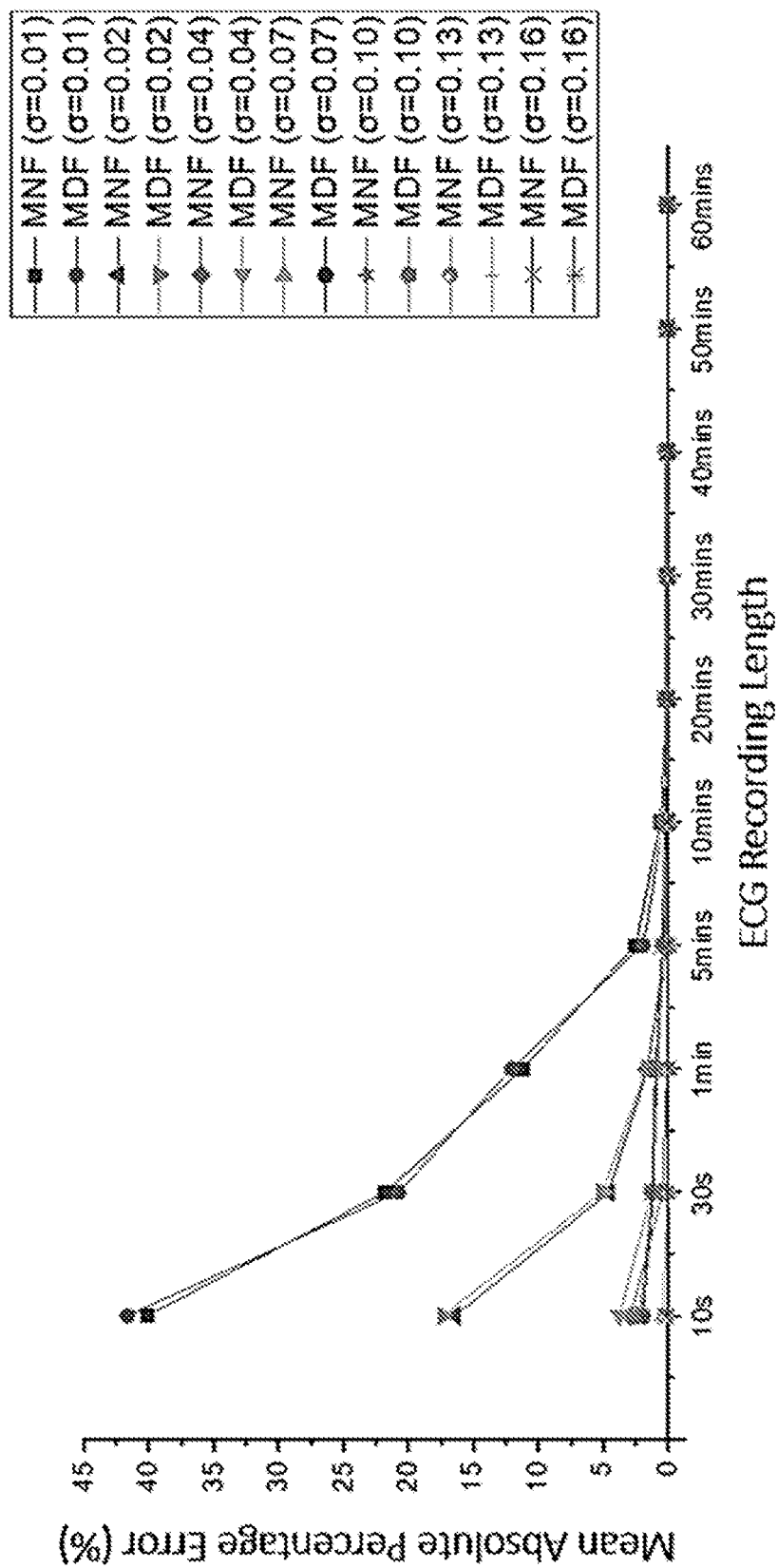
FIG. 10 is a graph showing the trend of the mean absolute error percentage (MAPE) of MNF and MDF between the PDS of simulated ECG and theoretical PDS for different values of a, HRV over different ECG lengths for an embodiment of the present invention.

As shown in FIG. 10, for the ultra-short segment length of 1 min, the maximal MAPEs of MNF and MDF were 11.21% and 12.04% respectively when a equaled to 0.01. The MAPEs of MNF and MDF decreased to 1.58% and 1.66% when a equaled to 0.02 and could be as low as 0.006% when σ equaled to 0.16. For the data segments that were shorter than 1-min long, the MAPEs of MNF and MDF increased especially for the small values of a. As shown in FIG. 9, the errors computed over the ECG data length of 10 s increase to 40.14% and 41.64% respectively for the MNF and MDF with the σ value of 0.01. It is clear from the results of simulation studies that the estimation accuracy of the frequency parameters MNF and MDF calculated over the ECG data length less than 30 s are sensitive to not only the data length but also the values of σ, and that the MAPEs calculated over the ECG data length of 1 min are less than 5% for the range of σ from 0.02 to 0.05. This range of such ultra-short term HRV a of RRIs is estimated from the clinical ECG recordings in PTBDB. Hence, it is reasonable to use the data of 1-min length for the PDS analysis and its frequency parameter estimation.

Figure 11:
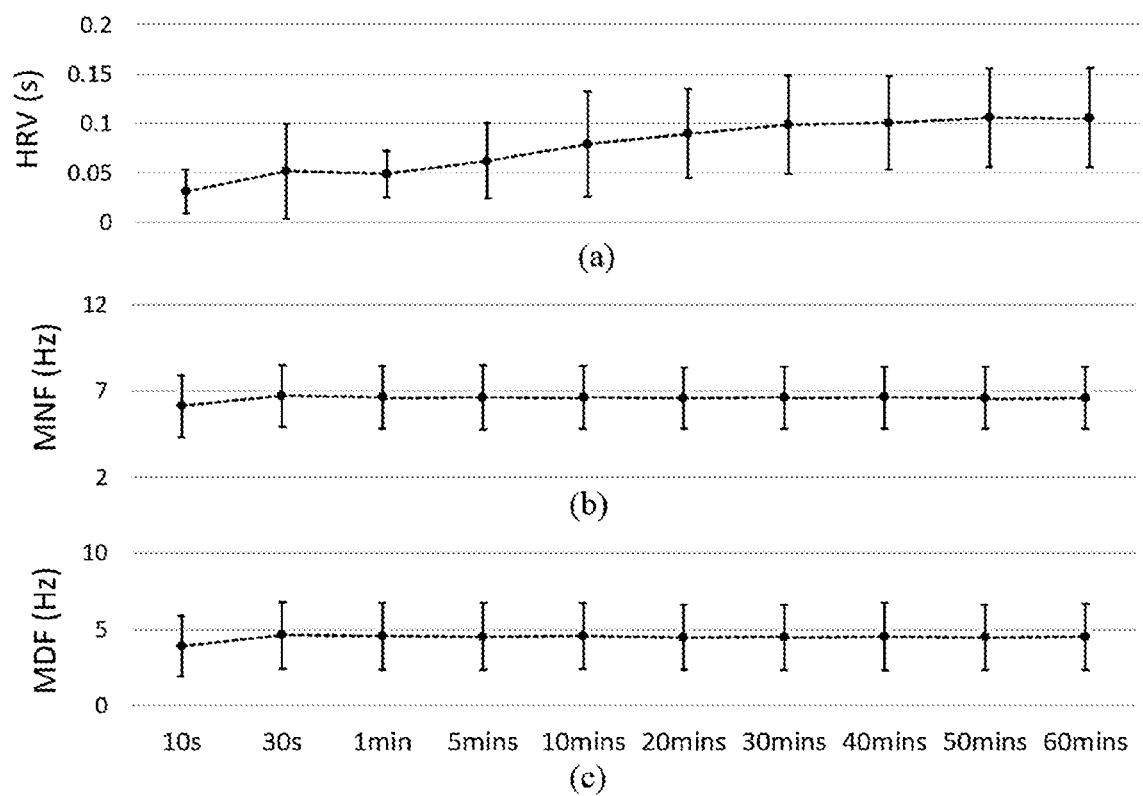
FIG. 11 is a graph showing the values of (a) HRV, (b) MNF and (c) MDF over different ECG lengths from 33 STEMI patients. The values are expressed as Mean±SD for an embodiment of the present invention.

FIG. 11 presents the values of HRV, MNF and MDF calculated on each randomly extracted segment of 10 s, 30 s, 1 min, 5 mins, 10 mins, 20 mins, 30 mins, 40 mins, 50 mins and 60 mins from 33 clinical ECG signals with ST-segment elevation in EDB. It can be seen from FIG.

11(a) that the HRV trended to increase with longer data lengths, which is consistent with the early study that demonstrated the longer recordings are associated with increased HRV. The statistical results showed that all the ultra-short-term HRVs (10 s, 30 s, 1 min) had significant differences compared with those calculated from 60-min data (p<0.0001). From FIGS. 11(b) and 11(c), it can be observed that the Mean±SD of MNF and MDF of 1 min data were 6.64±1.80 Hz and 4.54±2.20 Hz respectively, which were close with those of 60 mins (6.60±1.81 Hz and 4.50±2.16 Hz). The statistical results showed that there were no significant differences between MNF and MDF of 1 min and those of 60 mins (p=0.36; p=0.37). The MNF and MDF were relatively stable over the entire data lengths tested and showed no statistically significant differences in comparison with those calculated from the 60-min segments except for the segment length of 10 s. The results from the clinical ECGs indicated that although the length of the ECG recording will affect the HRV estimation, the MNF and MDF were nearly constant over the entire range of data lengths except for the segment of 10 s.

Step S104, alerting when the said indicators meet the preset abnormal conditions.

The alarm module of this application embodiment is used to alarm a patient with sudden ST-segment elevation myocardial infarction when the indicator information meets the preset conditions. The said present conditions include the range of the mean frequency of STEMI patients is approximate 5-9 Hz for ST-elevated leads and approximate 9-14 Hz for reference leads, and the mean frequency of healthy subjects is approximate 7-14 Hz and 8-13 Hz for normal leads which are corresponding to the ST-elevated leads and reference leads; and the range of the median frequency of STEMI patients is approximate 3-7 Hz for ST-elevated leads and approximate 7-13 Hz for reference leads; and the range of the median frequency of healthy subjects is approximate 5-12 Hz and 6-12 Hz for normal leads which are corresponding to the ST-elevated leads and reference leads etc. The invention will automatically alert for patients with sudden ST-segment elevation myocardial infarction in various way, such as sending local alarm bell to call for help, sending alarm information to emergency contacts and sending alarm messages to the emergency center etc. This application embodiment does not limit the specific alarm method, this application embodiment can alarm for sudden ST-segment elevation myocardial infarction patient, so that patients get timely assistance.

All the results of simulation and clinical studies strongly suggest that the MNF and MDF with the minimal effects of HR and HRV but instead they are dominated by morphological changes in P-QSR-T complexes. The proposed frequency parameters obtained from ultra-short-term ECG of 60 s (or even shorter to 30 s) can differentiate the STEMI patients from healthy subjects with the same level of accuracy achieved by the frequency parameters over longer ECG signals of 60 mins, which provided the possibility of using the ultra-short-term frequency parameters in wearable devices and its applications in wearable based-mHealth to qualitatively measure the frequency shift phenomena for the diagnosis of STEMI diseases.

According to a detailed aspect of the invention, potential parameters are proposed by quantifying the consistent frequency shift phenomenon between the PDSs of ST-elevated lead and reference lead with and without ST-elevation from the same patient to differentiate the STEMI patients from healthy subjects. Wherein the mean frequency (MNF) and median frequency (MDF) of the PDSs of the ECG signals are two potential indicators for the diagnosis of STEMI proposed in this application embodiment; the other two parameters are the mean frequency shift ratio and the median frequency shift ratio.

The invention also includes computer simulation, the simulated ECG are generated by convoluting the Gaussian distributed PPT with P-QRS-T complex, which is randomly extracted from a cycle of the clinical ECG recordings by eyeballing. The invention includes the ECG simulation with a given P-QRS-T waveform and various values of HR and HRV in the physiological range, which is performed to systematically investigate their effects on the proposed parameters identified in the frequency domain of proposed new parameters between theoretical and simulated ECG data. Additionally, the new parameters were also studied on different segment lengths of clinical ECG recordings with ST-segment elevation to investigate the effects of the length of ECG recording and the reliability of the new indicators in ultra-short-term ECG recordings.

The invention includes a mathematical model for ECG signal generation which is proposed with the P-QRS-T complexes as the impulse response of a linear time-invariant system and a pacing pulse train (PPT) with random R-R intervals (RRIs) mimicking the S-A node fittings as the input to the system. Based on the model, the equations showing the interactive effects of heart rate (HR), its variability and P-QRS-T complexes on the PDS of ECG signal are derived. Additionally, the PDS analysis of clinical ECG recordings of healthy subjects and STEMI patients from existing databases is carried out to verify the theoretical results and to study possible indicators for the diagnosis of STEMI diseases based on the statistical analysis.

According to the simulation and clinical analysis, the results showed that the changes in proposed frequency parameters caused by HR and HRV are relatively small, and instead they are dominated by morphological changes in P-QSR-T complexes. Additionally, the proposed frequency parameters obtained from ultra-short-term ECG of 60 s can differentiate the STEMI patients from healthy subjects with the same level of accuracy achieved by the frequency parameters over longer ECG signals of 60 mins, which provided the possibility of using the ultra-short-term frequency parameters in wearable devices to become a powerful tool for the detection, diagnosis, monitoring, management, and study of STEMI and other cardiovascular diseases through qualitatively measuring the frequency shift phenomena.

The present application embodiment provides a possible way to study and verify the said ECG frequency parameters to get the analytical validation results, including:
 the ECG frequency parameters are analyzed and verified by the interactive effect level of HR, HRV and P-QRS-T complexes to obtain the analytical validation results.

The simulated ECG are generated by convoluting the Gaussian distributed PPT with P-QRS-T complex, which is randomly extracted from a cycle of the clinical ECG recordings by eyeballing. The invention includes the ECG simulation with a given P-QRS-T waveform and various values of HR and HRV in the physiological range, which is performed to systematically investigate their effects on the proposed parameters identified in the frequency domain of proposed new parameters between theoretical and simulated ECG data. Additionally, the new parameters were also studied on different segment lengths of clinical ECG recordings with ST-segment elevation to investigate the effects of the length of ECG recording and the reliability of the new indicators in ultra-short-term ECG recordings.

Clinical analysis and computer simulations verified the correctness and feasibility of the proposed mathematical model, and the observed results of the power spectrum of the ECG signal could be explained by the interactive effects of HR, HRV and P-QRS-T waveforms. According to the clinical analysis, the proposed frequency parameters, MNF, MDF and their shift ratios showed significant differences between STEMI patients and healthy subjects.

According to the simulation and clinical analysis, the results showed that the changes in proposed frequency parameters caused by HR and HRV are relatively small, and instead they are dominated by morphological changes in P-QSR-T complexes. Additionally, the proposed frequency parameters obtained from ultra-short-term ECG of 60 s can differentiate the STEMI patients from healthy subjects with the same level of accuracy achieved by the frequency parameters over longer ECG signals of 60 mins, which provided the possibility of using the ultra-short-term frequency parameters in wearable devices to become a powerful tool for the detection, diagnosis, monitoring, management, and study of STEMI and other cardiovascular diseases through qualitatively measuring the frequency shift phenomena.

Embodiments of the present application provide a possible way of implementing, the subjects include positive sample objects and negative sample objects. The negative sample subjects are patients with ST-segment elevation myocardial infarction and the positive sample are healthy subjects.

Sample objects of this application embodiment include positive sample objects and negative sample objects. The negative sample subjects are patients with ST-segment elevation myocardial infarction and the positive sample are healthy subjects.

The ECG signals of the subjects obtained through designed electrodes include obtaining the ECG signals of STEMI patients from the ST-elevated leads in terms of the ischemic area and from reference leads without ST-segment elevation through designed electrodes.

The frequency range of useful information in the ECG signal of this application embodiment is approximately 0.05-100 Hz. In order to evaluate and quantify the power distributions showed in the PDSs of ECG signals with different HRs, HRVs and P-QRS-T complexes, MNF and MDF of PDSs are calculated from 0.05 Hz to 100 Hz. The leads without ST-segment elevation in STEMI patients are regarded as reference leads. Another parameter is the frequency shift ratio of MNF or MDF, which is defined as the quotient of the difference in the frequency parameters between the reference lead and the ST-elevated lead divided by the frequency parameter of the reference lead.

Obtaining the ECG signals of healthy subjects from the normal leads which are corresponding to the ST-elevated leads and reference leads of STEMI patients through designed electrodes.

The ECG PDSs of healthy subjects in this application embodiment is calculated from the normal leads corresponding to the ST-elevated leads and the reference leads of the STEMI patient.

Embodiments of the present application provide a possible way of implementing, the proposed ECG frequency parameters are computed from the ECG power density spectra of two leads from the same subject, and at least one of the frequency parameters and frequency shift ratios are obtained by quantifying the frequency distribution phenomena in the PDSs.

The ECG frequency parameters in this application include at least one of mean frequency, median frequency.

The ECG frequency parameters in this application include at least one of mean frequency shift ratio and median frequency shift ratio.

Embodiments of the present application provide a possible way of implementing, the ECG frequency parameters in this application include at least one of mean frequency, median frequency, mean frequency shift ratio and median frequency shift ratio.

It should be noted that the frequency components of the ECG signal is calculated in the median division in this application embodiment to obtain the median frequency and the median frequency shift ratio, which is only an implementable way, and the frequency components of the ECG signal is calculated using other division methods, such as 30%, 70% or 40%, 60%, to obtain the corresponding percentage of frequency value and ratio, which is also within the scope of protection of this application and will not be limited here.

The mean frequency in the application, is calculated from the PDSs of the STEMI patients and healthy subjects, which can be used to differentiate STEMI patients and healthy subjects.

The median frequency in the application, is calculated from the PDSs of the STEMI patients and healthy subjects, which can be used to differentiate STEMI patients and healthy subjects.

The mean frequency shift ratio is calculated from the PDSs of the STEMI patients and healthy subjects, which can be used to differentiate STEMI patients and healthy subjects; The mean frequency or median frequency can be defined as the quotient of the difference in the frequency parameters between the reference lead and the ST-elevated lead divided by the frequency parameter of the reference lead.

Embodiments of the present application provide a possible way of implementing, the mean frequency can be used to characterize the degree of differentiation between STEMI patients and healthy subjects, and the median frequency is used to characterize the degree of differentiation between STEMI patients and healthy subjects.

The range of the mean frequency of STEMI patients is approximate 5-9 Hz for ST-elevated leads and approximate 9-14 Hz for reference leads; and the mean frequency of healthy subjects is approximate 7-14 Hz and 8-13 Hz for normal leads which are corresponding to the ST-elevated leads and reference leads.

The range of the median frequency of STEMI patients is approximate 3-7 Hz for ST-elevated leads and approximate 7-13 Hz for reference leads; and the range of the median frequency of healthy subjects is approximate 5-12 Hz and 6-12 Hz for normal leads which are corresponding to the ST-elevated leads and reference leads.

Embodiments of the present application provide a possible way of implementing, the mean frequency shift ratio can be used to characterize the degree of differentiation between STEMI patients and healthy subjects, and the median frequency shift ratio can be used to characterize the degree of differentiation between STEMI patients and healthy subjects.

Wherein the mean frequency can be defined as the quotient of the difference in the mean frequency between the reference lead and the ST-elevated lead divided by the mean frequency of the reference lead; the median frequency can be defined as the quotient of the difference in the median frequency between the reference lead and the ST-elevated lead divided by the median frequency of the reference lead.

The mean frequency shift ratio and median frequency shift ratio in the application is calculated from the PDSs of the STEMI patients and healthy subjects, which can be used to differentiate STEMI patients and healthy subjects; The mean frequency or median frequency can be defined as the quotient of the difference in the frequency parameters between the reference lead and the ST-elevated lead divided by the frequency parameter of the reference lead.

Details are given in the following equations.

$$MDF \text{ shift ratio} = \frac{MDF_{reference} - MDF_{ST-elevated\ lead}}{MDF_{reference}}$$

$$MNF \text{ shift ratio} = \frac{MNF_{reference} - MNF_{ST-elevated\ lead}}{MNF_{reference}}$$

Embodiments of the present application provide a possible way of implementing, the range of the mean frequency of STEMI patients is approximate 5-9 Hz for ST-elevated leads and approximate 9-14 Hz for reference leads; and the mean frequency of healthy subjects is approximate 7-14 Hz and 8-13 Hz for normal leads which are corresponding to the ST-elevated leads and reference leads.

Embodiments of the present application provide a possible way of implementing, the range of the median frequency of STEMI patients is approximate 3-7 Hz for ST-elevated leads and approximate 7-13 Hz for reference leads; and the range of the median frequency of healthy subjects is approximate 5-12 Hz and 6-12 Hz for normal leads which are corresponding to the ST-elevated leads and reference leads.

Embodiments of the present application provide a possible way of implementing, the mean frequency shift ratio and median frequency shift ratio are approximate 20-50% and 35-65% for STEMI patient while the mean frequency shift ratio and median frequency shift ratio in healthy subjects are below a predetermined threshold and the predetermined threshold comprises 0.

Embodiments of the present application provide a possible way of implementing, the ECG frequency parameters are studied and verified to get the analytical validation results, including:

when the range of the ECG PDSs of subjects are within the first frequency range, the ECG frequency parameters are affected by HR and HRV at a lower level than the first impact level threshold. The ECG frequency parameters are more depended on the P-QRS-T complexes, which reflect the abnormal cardiac condition caused by abnormal cardiac contraction dynamics resulting in the changes of the P-QRS-T complexes;

when the range of the ECG PDSs of subjects are within the second frequency range, the ECG frequency parameters are affected by HR and HRV at a higher level than the second impact level threshold. The ECG frequency parameters can reflect the interactive effects of the HR, HRV and P-QRS-T complexes and the changes of the ECG frequency parameters over different ECG signal lengths are below a predetermined degree of change threshold.

The ECG frequency parameters in this application embodiment reflect not only the abnormal cardiac contraction but also the lesions that occur with abnormal electrical impulse conduction.

Embodiments of the present application provide a possible way of implementing, the ratio of power in the first two peaks to the power in the first frequency range or second frequency range can be used to characterize the degree of differentiation between STEMI patients and healthy subjects, wherein the ratio in ST-elevated leads is larger than the ratio in reference leads of STEMI patient while the ratios in the two normal leads of healthy subjects are nearly identical.

Embodiments of the present application provide a possible way of implementing, the first frequency range specifically includes 0.05-100 Hz.

When the frequency parameters are calculated from the PDS in the range of 0.05-100 Hz in this application embodiment, the ECG frequency parameters are less affected by HR and HRV and more depended on the P-QRS-T complexes and the frequency parameters are relatively stable over different tested ECG lengths through clinical ECG signal analysis.

Embodiments of the present application provide a possible way of implementing, the second frequency range is smaller than the first frequency range.

When the parameters calculated from the smaller range, the frequency parameters can reflect the interactive effects of the HR, HRV and P-QRS-T complexes. Hence for other abnormal cardiac conditions mainly caused by abnormal heart rhythm statistics such as arrhythmia, tachycardia, bradycardia, the parameters calculated from the range can not only reflect the effects of heart rhythm statistics but the P-QRS-T complexes associated with the cardiac contraction dynamics as well. It means that different calculation ranges of the parameters can reflect different dominated effects of abnormal cardiac condition.

(1) when the calculation range of the ECG PDSs of subjects is relatively wide, the ECG frequency parameters are less affected by HR and HRV but more depended on the P-QRS-T complexes, which reflect the abnormal cardiac condition caused by abnormal cardiac contraction dynamics resulting in the changes of the P-QRS-T complexes;

(2) when the calculation range of the ECG PDSs of subjects is relatively small, the ECG frequency parameters can reflect the interactive effects of the HR, HRV and P-QRS-T complexes which can not only reflect the abnormal heart contraction, but also the lesions that occur with abnormal electrical impulse conduction;

Embodiments of the present application provide a possible way of implementing, the designed electrodes include at least one of flexible electrodes, dry electrodes, wet electrodes, and textile electrodes.

The predetermined electrode of this application embodiment may be any electrode that can capture the ECG signal of the sample subject, for example, it may be at least one or a combination of at least one of flexible electrode, dry electrode, wet electrode and textile electrode, and this application embodiment does not limit the material of the electrode that captures the ECG signal of the sample subject.

Embodiments of the present application provide a possible way of implementing, the alerting includes sending local alarm bell to call for help; ending alarm information to emergency contacts; sending alarm messages to the emergency center.

The alarm module specifically includes (1) local alarm bell to call for help, which can be heard by people in the surrounding area for emergency rescue; (2) sending alarm information to emergency contacts, which will be sent to the pre-set emergency contacts' cell phones, tablets, laptops, PDAs, car terminals, wearable devices and other devices in a timely manner, (3) sending alarm information to emergency centers (3) send alarm information to emergency centers, such as 120, 999, etc., so that patients with sudden myocardial infarction can receive timely assistance.

Figure 12:
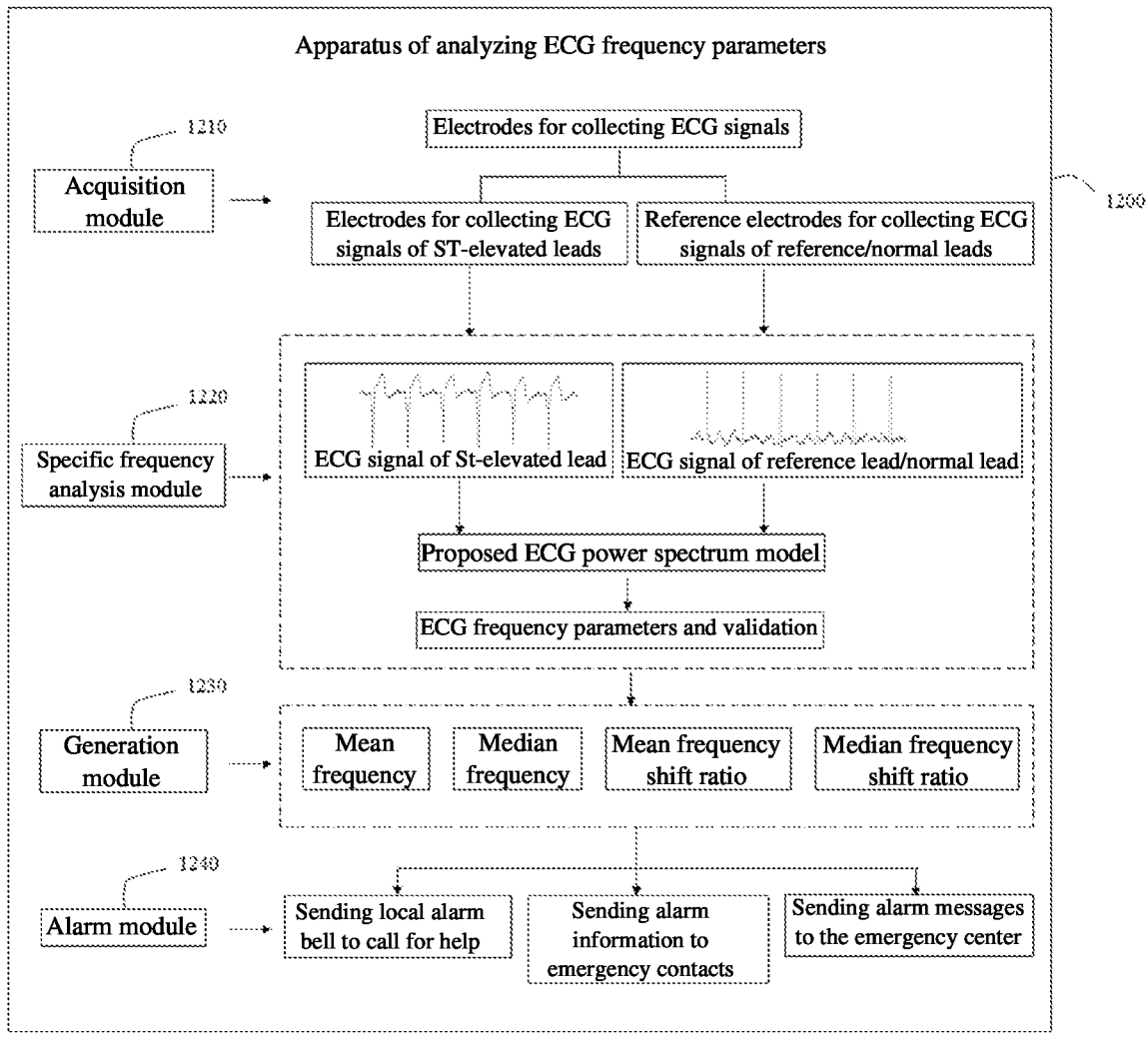
FIG. 12 is a schematic diagram of the apparatus for analyzing ECG frequency parameters provided in an embodiment of the present invention.

Embodiments of the present application provide an ECG frequency parameters analysis apparatus 1200, as shown in FIG. 12, which comprises: acquisition module 1210, which is used for obtaining ECG signals from subjects through the designed electrodes; the ECG signals include the ECG signals of ST-elevated leads, the ECG signals of reference leads without ST-segment elevation from STEMI patients or ECG signals of normal leads from healthy subjects; The designed electrodes include at least one of flexible electrodes, dry electrodes, wet electrodes and textile electrodes; frequency analysis module 1220, which is used for calculating the ECG frequency domain parameters of the subjects based on the proposed power spectrum model and getting the analytical validation results after studying and verifying the parameters; generation module 1230, which is used for generating indicators based on the analytical validation results and they could be potentially used as alternative indicators for STEMI diagnosis; and alarm module 1240, which will alert when the indicators meet the preset abnormal conditions. The present embodiment is a powerful tool to diagnose STEMI diseases faster and more effectively and helps patients receive timely assistance and treatment.

The specific implementation steps are the same as the above-mentioned ECG frequency parameter analysis method, and will not be repeated here, as described in detail in the above-mentioned ECG frequency parameter analysis method.

Embodiments of the present application provide a possible way of implementing, wherein the frequency analysis module is specifically used for calculating the ECG signals of the subjects based on the proposed power spectrum model to get the ECG frequency domain parameters. The ECG frequency parameters are analyzed and verified by the interactive effect level of HR, HRV and P-QRS-T complexes to obtain the analytical validation results.

Embodiments of the present application provide a possible way of implementing, wherein the subjects include positive sample objects and negative sample objects. The negative sample subjects are patients with ST-segment elevation myocardial infarction and the positive sample are healthy subjects.

The acquisition module comprises a first acquisition unit and a second acquisition unit; the first acquisition unit, which is used for obtaining the ECG signals of STEMI patients from the ST-elevated leads in terms of the ischemic area and from reference leads without ST-segment elevation through designed electrodes; the second acquisition unit, which is used for obtaining the ECG signals of healthy subjects from the normal leads and they are corresponding to the ST-elevated leads and reference leads of STEMI patients.

Embodiments of the present application provide a possible way of implementing, the proposed ECG frequency parameters are computed from the ECG power density spectra of two leads from the same subject, and at least one of the frequency parameters and frequency shift ratios are obtained by quantifying the frequency distribution phenomena in the PDSs.

Embodiments of the present application provide a possible way of implementing, the ECG frequency parameters include at least one of mean frequency, median frequency, mean frequency shift ratio and median frequency shift ratio.

Embodiments of the present application provide a possible way of implementing, the mean frequency is used to characterize the degree of differentiation between STEMI patients and healthy subjects, and the median frequency is used to characterize the degree of differentiation between STEMI patients and healthy subjects.

Embodiments of the present application provide a possible way of implementing, the mean frequency shift ratio and/or the median frequency shift ratio can be used for characterizing the degree of differentiation between STEMI patients and healthy subjects; wherein the mean frequency shift ratio is defined as the quotient of the difference in the frequency parameters between the reference lead and the ST-elevated lead divided by the frequency parameter of the reference lead; and the median frequency shift ratio is defined as the quotient of the difference in the frequency parameters between the reference lead and the ST-elevated lead divided by the frequency parameter of the reference lead.

Embodiments of the present application provide a possible way of implementing, wherein the range of the mean frequency of STEMI patients is approximate 5-9 Hz for ST-elevated leads and approximate 9-14 Hz for reference leads; and the mean frequency of healthy subjects is approximate 7-14 Hz and 8-13 Hz for normal leads which are corresponding to the ST-elevated leads and reference leads.

Embodiments of the present application provide a possible way of implementing, wherein the range of the median frequency of STEMI patients is approximate 3-7 Hz for ST-elevated leads and approximate 7-13 Hz for reference leads; and the range of the median frequency of healthy subjects is approximate 5-12 Hz and 6-12 Hz for normal leads which are corresponding to the ST-elevated leads and reference leads.

Embodiments of the present application provide a possible way of implementing, wherein the mean frequency shift ratio and median frequency shift ratio are approximate 20-50% and 35-65% for STEMI patient while the mean frequency shift ratio and median frequency shift ratio in healthy subjects are below a predetermined threshold and the predetermined threshold comprises 0.

Embodiments of the present application provide a possible way of implementing, when the range of the ECG PDSs of subjects are within the first frequency range, the ECG frequency parameters are affected by HR and HRV at a lower level than the first impact level threshold. The ECG frequency parameters are more depended on the P-QRS-T complexes, which reflect the abnormal cardiac condition caused by abnormal cardiac contraction dynamics resulting in the changes of the P-QRS-T complexes.

When the range of the ECG PDSs of subjects are within the second frequency range, the ECG frequency parameters are affected by HR and HRV at a higher level than the second impact level threshold. The ECG frequency parameters can reflect the interactive effects of the HR, HRV and P-QRS-T complexes and the changes of the ECG frequency parameters over different ECG signal lengths are below a predetermined degree of change threshold.

Embodiments of the present application provide a possible way of implementing, the ratio of power in the first two peaks to the power in the first frequency range or second frequency range can be used to characterize the degree of differentiation between STEMI patients and healthy subjects; wherein the ratio in ST-elevated leads is larger than the ratio in reference leads of STEMI patient while the ratios in the two normal leads of healthy subjects are nearly identical.

Embodiments of the present application provide a possible way of implementing, the first frequency range specifically includes 0.05-100 Hz.

Embodiments of the present application provide a possible implementation, the designed electrodes include at least one of flexible electrodes, dry electrodes, wet electrodes and textile electrodes.

Embodiments of the present application provide a possible way of implementing, the second frequency range is smaller than the first frequency range.

Embodiments of the present application provide a possible way of implementing, the designed electrodes include at least one of flexible electrodes, dry electrodes, wet electrodes, and textile electrodes.

Embodiments of the present application provide a possible way of implementing, the alarm module includes sending local alarm bell to call for help; sending alarm information to emergency contacts; sending alarm messages to the emergency center.

The specific implementation steps are the same as those described above for the ECG frequency parameter analysis apparatus, and will not be repeated here, as described above for the ECG frequency parameter analysis apparatus.

An electronic apparatus is provided in this application embodiment comprising, a memory and a processor, at least one program, stored in the memory for execution by the processor when compared to the prior art: obtaining ECG signals from sample objects and calculating the ECG frequency parameters of the subjects based on the proposed power spectrum model and getting the analytical validation results after studying and verifying the parameters; generating indicators based on the analytical validation results, which could be potentially used as alternative indicators for STEMI diagnosis; and alerting when the indicators meet the preset abnormal conditions. The present embodiment is a powerful tool to diagnose STEMI diseases faster and more effectively and helps patients receive timely assistance and treatment.

Figure 13:
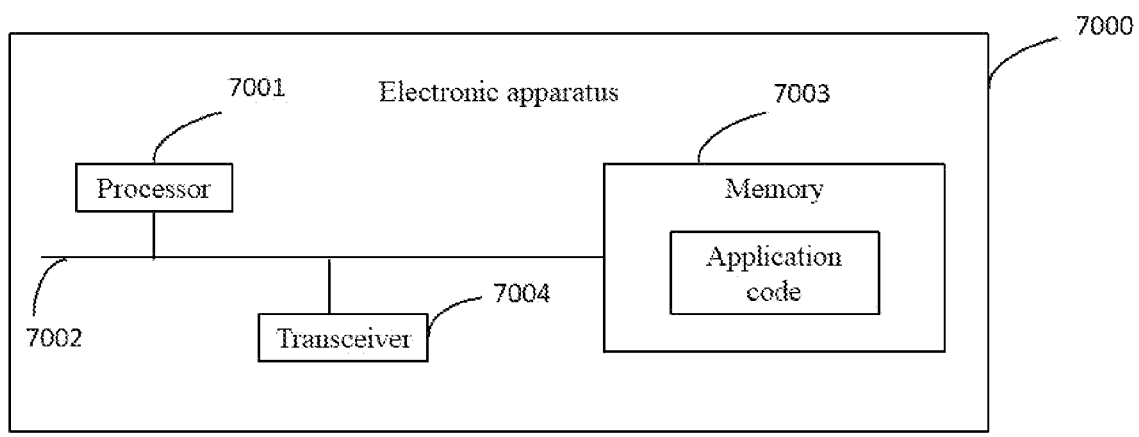
FIG. 13 is a schematic diagram of the structure of the electronic apparatus provided in an embodiment of the present invention.

In an optional embodiment an electronic apparatus is provided, as shown in FIG. 13, the electronic apparatus 7000 shown in FIG. 13 comprises: a processor 7001 and a memory 7003. wherein the processor 7001 and the memory 7003 are connected, e.g. via a bus 7002. Optionally, the electronic apparatus 7000 may also include a transceiver 7004. It is noted that the transceiver 7004 is not limited to one in practical applications, and the structure of the electronic apparatus 7000 does not constitute a limitation of this application embodiment.

The processor 7001 may be a Central Processing Unit (CPU), a general-purpose processor, a Digital Signal Processor (DSP), an Application Specific Integrated Circuit (ASIC), an Field Programmable Gate Array (FPGA), or other programmable logic device, transistorized logic device, hardware component, or any combination thereof. It may implement or execute various exemplary logic boxes, modules, and circuits described in conjunction with the disclosure of this application. Processor 7001 may also be a combination that implements a computing function, such as a combination containing one or more microprocessors, a combination of a DSP and a microprocessor, etc.

The bus 7002 may include a pathway to transfer information between the above components. The bus 7002 may be a Peripheral Component Interconnect (PCI) bus or an Extended Industry Standard Architecture (EISA) bus, for example. The bus 7002 can be divided into address bus, data bus, control bus, etc. For the convenience of representation, only one thick line is used in FIG. 13, but it does not mean that there is only one bus or one type of bus.

The memory 7003 may be a Read Only Memory (ROM) or other type of static storage device that can store static information and instructions, a Random Access Memory (RAM) or other type of dynamic storage device that can store information and instructions, or an Electrically Erasable Programmable Read Only Memory (EEPROM), Compact Disc Read Only Memory (CD-ROM) or other optical disc storage, optical disc storage (including compressed disc, laser disc, optical disc, digital universal CD-ROM or other optical disc storage, optical disc storage (including compact disc, laser disc, optical disc, digital universal disc, Blu-ray disc, etc.), disk storage media or other magnetic storage devices, or any other media capable of carrying or storing desired program code in the form of instructions or data structures and capable of being accessed by a computer, but not limited thereto.

The memory 7003 is used to store application program code for executing the present application solution and is controlled for execution by the processor 7001. The processor 7001 is used to execute the application program code stored in the memory 7003 to implement what is shown in the preceding method embodiment.

It will be understood by those skilled in the art that the structure of the electronic apparatus illustrated in FIG. 13 does not constitute a limitation of the electronic apparatus, and that the electronic apparatus may include more or fewer components than illustrated, or a combination of certain components, or a different arrangement of components.

In embodiments of the present invention, the electronic apparatus includes, but is not limited to, a cell phone, a tablet computer, a laptop computer, a handheld computer, a vehicle terminal, a wearable device, and a pedometer, among others.

Embodiments of the present application provide a computer readable storage medium having a computer program stored on the computer readable storage medium that, when run on the computer, enables the computer to execute the corresponding contents of the foregoing method embodiments. Compared to prior art, obtaining ECG signals from subjects and calculating the ECG frequency parameters of the subjects based on the proposed ECG power spectrum model and getting the analytical validation results after studying and verifying the parameters; generating indicators based on the analytical validation results, which could be potentially used as alternative indicators for STEMI diagnosis; and alerting when the indicators meet the preset abnormal conditions. The present embodiment is a powerful tool to diagnose STEMI diseases faster and more effectively and helps patients receive timely assistance and treatment.

Embodiments of the present application provide a computer program comprising computer instructions, the computer instructions being stored in a computer readable storage medium, and when a processor of the computer device reads the computer instructions from the computer readable storage medium, the processor executes the computer instructions such that the computer device performs as shown in the preceding method embodiment. Compared to existing technology, obtaining ECG signals from sample objects; calculating the ECG frequency parameters of the subjects based on the proposed power spectrum model and getting the analytical validation results after studying and verifying the parameters; generating indicators based on the analytical validation results, which could be potentially used as alternative indicators for STEMI diagnosis; and alerting when the indicators meet the preset abnormal conditions. The present embodiment is a powerful tool to diagnose STEMI diseases faster and more effectively and helps patients receive timely assistance and treatment.

It should be understood that although the steps in the attached flowchart are shown in sequence as indicated by the arrows, they are not necessarily carried out in the order indicated by the arrows. Unless explicitly stated in this article, there is no strict order in which these steps can be performed, and they can be performed in any other order. Moreover, at least part of the steps in the attached flowchart may include multiple sub-steps or stages. These sub-steps or stages are not necessarily executed at the same time, but can be executed at different times, and their execution sequence is not necessarily sequential. It may be performed alternately or alternately with other steps or at least part of a substep or phase of another step.

Above is only part of the present invention, it should be pointed out that for the ordinary technical personnel in the field of technology, on the premise of not out of the present invention principle, also can make some improvements and retouching, these improvements and polishing also shall be regarded as the protection range of the present invention. The present description illustrates the principles of the present invention. It will thus be appreciated that those skilled in the art will be able to devise various arrangements that, although not explicitly described or shown herein, embody the principles of the invention and are included within its spirit and scope.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

While the invention has been illustrated and described in detail in the drawings and foregoing description, the same is to be considered as illustrative and not restrictive in character, it being understood that only exemplary embodiments have been shown and described and do not limit the scope of the invention in any manner. It can be appreciated that any of the features described herein may be used with any embodiment. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art.

The invention claimed is:

1. A method of analyzing ECG frequency parameters, the method comprising:
   obtaining ECG signals from subjects through electrodes; the ECG signals include ECG signals of ST-elevated leads, ECG signals of reference leads without ST-segment elevation from STEMI patients or ECG signals of normal leads from healthy subjects;
   calculating ECG frequency domain parameters of the subjects based on an ECG power spectrum model and getting analytical validation results after studying and verifying the parameters;
   generating indicators based on the analytical validation results for use as alternative indicators for STEMI diagnosis; and
   alerting when the indicators meet preset abnormal conditions.

2. The method in accordance with claim 1, wherein the ECG frequency domain parameters are studied and verified to get the analytical validation results, including:
   the ECG frequency domain parameters are analyzed and verified by interactive effects of HR, HRV and P-QRS-T complexes to obtain the analytical validation results.

3. The method in accordance with claim 2, wherein the ECG frequency domain parameters are studied and verified to get the analytical validation results, including:
   when a range of the ECG PDSs of subjects is within a first frequency range, the ECG frequency domain parameters are affected by HR and HRV at a lower level than a first impact level threshold; the ECG frequency domain parameters are depended on P-QRS-T complexes, which reflect abnormal cardiac condition caused by abnormal cardiac contraction dynamics resulting in changes of the P-QRS-T complexes;
   when the range of the ECG PDSs of subjects is within a second frequency range, the ECG frequency domain parameters are affected by HR and HRV at a higher level than a second impact level threshold; the ECG frequency domain parameters reflect the interactive effects of the HR, HRV and P-QRS-T complexes and changes of the ECG frequency domain parameters over different ECG signal lengths are below a predetermined degree of change threshold.

4. The method in accordance with claim 3, the first frequency range includes 0.05-100 Hz; and the second frequency range is smaller than the first frequency range.

5. The method in accordance with claim 1, wherein the subjects include positive sample objects and negative sample objects, the negative sample subjects being patients with ST-segment elevation myocardial infarction and the positive sample being healthy subjects;
   the ECG signals of the subjects obtained through the electrodes include:
      obtaining the ECG signals of STEMI patients from the ST-elevated leads in terms of ischemic area and from reference leads without ST-segment elevation through the electrodes;
      obtaining the ECG signals of healthy subjects from the normal leads which are corresponding to the ST-elevated leads and the reference leads of STEMI patients.

6. The method in accordance with claim 1, the ECG frequency domain parameters are computed from an ECG power density spectra of two leads from the same subject, and at least one of the ECG frequency domain parameters and frequency shift ratios are obtained by quantifying frequency distribution phenomena in PDSs.

7. The method in accordance with claim 6, the ECG frequency domain parameters include at least one of a mean frequency, a median frequency, a mean frequency shift ratio and a median frequency shift ratio; the mean frequency characterizes a degree of differentiation between STEMI patients and healthy subjects, and the median frequency characterizes the degree of differentiation between STEMI patients and healthy subjects.

8. The method in accordance with claim 7, the mean frequency shift ratio and/or the median frequency shift ratio characterize the degree of differentiation between STEMI patients and healthy subjects; wherein the mean frequency shift ratio is defined as quotient of difference in the mean frequency between the reference lead and the ST-elevated lead divided by the mean frequency of the reference lead; and the median frequency shift ratio is defined as quotient of difference in the median frequency between the reference lead and the ST-elevated lead divided by the median frequency of the reference lead.

9. The method in accordance with claim 7, wherein range of the mean frequency of STEMI patients is approximate 5-9 Hz for the ST-elevated leads and approximate 9-14 Hz for the reference leads; and the mean frequency of healthy subjects is approximate 7-14 Hz and 8-13 Hz for the normal leads which are corresponding to the ST-elevated leads and the reference leads;
range of the median frequency of STEMI patients is approximate 3-7 Hz for the ST-elevated leads and approximate 7-13 Hz for the reference leads; and range of the median frequency of healthy subjects is approximate 5-12 Hz and 6-12 Hz for the normal leads which are corresponding to the ST-elevated leads and the reference leads; and the mean frequency shift ratio and the median frequency shift ratio are approximate 20-50% and 35-65% for STEMI patient while the mean frequency shift ratio and the median frequency shift ratio in healthy subjects are below a predetermined threshold of 0.

10. The method in accordance with claim 6, ratio of power in first two peaks to power in the first frequency range or the second frequency range is used to characterize the degree of differentiation between STEMI patients and healthy subjects; wherein the ratio in ST-elevated leads is larger than the ratio in reference leads of STEMI patient while the ratios in the two normal leads of healthy subjects are nearly identical.

11. The method in accordance with claim 1, the alerting includes:
sending a local alarm bell to call for help;
sending an alarm information to emergency contacts;
sending alarm messages to an emergency center.

12. An electronic apparatus, comprising a memory, a processor, and a computer program stored in the memory and running on the processor, wherein the processor executes the program to implement the steps of the analysis method of claim 1.

13. An apparatus of analyzing ECG frequency parameters, the apparatus comprising:
acquisition module for obtaining ECG signals from subjects through electrodes; the ECG signals include ECG signals of ST-elevated leads, ECG signals of reference leads without ST-segment elevation from STEMI patients or ECG signals of normal leads from healthy subjects;
frequency analysis module for calculating ECG frequency domain parameters of the subjects based on an ECG power spectrum model and getting analytical validation results after studying and verifying the parameters;
generation module for generating indicators based on the analytical validation results for used as alternative indicators for STEMI diagnosis; and
alarm module which alerts when the indicators meet preset abnormal conditions.

14. The apparatus in accordance with claim 13, wherein the frequency analysis module calculates the ECG signals of the subjects based on the ECG power spectrum model to get the ECG frequency domain parameters; the ECG frequency domain parameters are analyzed and verified by interactive effects of HR, HRV and P-QRS-T complexes to obtain the analytical validation results.

15. The apparatus in accordance with claim 14, wherein the frequency analysis module is used for:
when a range of the ECG PDSs of subjects is within a first frequency range, the ECG frequency domain parameters are affected by HR and HRV at a lower level than a first impact level threshold; the ECG frequency domain parameters are depended on P-QRS-T complexes, which reflect abnormal cardiac condition caused by abnormal cardiac contraction dynamics resulting in changes of the P-QRS-T complexes;
when range of the ECG PDSs of subjects is within a second frequency range, the ECG frequency domain parameters are affected by HR and HRV at a higher level than a second impact level threshold; the ECG frequency domain parameters reflect the interactive effects of the HR, HRV and P-QRS-T complexes and changes of the ECG frequency domain parameters over different ECG signal lengths are below a predetermined degree of change threshold.

16. The apparatus in accordance with claim 13, wherein the subjects include positive sample objects and negative sample objects; the negative sample subjects being patients with ST-segment elevation myocardial infarction and the positive sample being healthy subjects; the acquisition module comprises a first acquisition unit and a second acquisition unit; the first acquisition unit obtains the ECG signals of STEMI patients from the ST-elevated leads in terms of ischemic area and from the reference leads without ST-segment elevation through the electrodes; the second acquisition unit obtains the ECG signals of healthy subjects from the normal leads correspond to the ST-elevated leads and the reference leads of STEMI patients.

17. The apparatus in accordance with claim 13, the ECG frequency domain parameters are computed from an ECG power density spectra of two leads from the same subject, and at least one of the frequency parameters and frequency shift ratios are obtained by quantifying frequency distribution phenomena in PDSs.

18. The apparatus in accordance with claim 17, the ECG frequency domain parameters include at least one of a mean frequency, a median frequency, a mean frequency shift ratio and a median frequency shift ratio; wherein the mean frequency characterizes a degree of differentiation between STEMI patients and healthy subjects, and the median frequency characterizes the degree of differentiation between STEMI patients and healthy subjects.

19. The apparatus in accordance with claim 18, the mean frequency shift ratio and/or the median frequency shift ratio characterize the degree of differentiation between STEMI patients and healthy subjects; wherein the mean frequency shift ratio is defined as quotient of difference in the mean frequency between the reference lead and the ST-elevated lead divided by the mean frequency of the reference lead; and the median frequency shift ratio is defined as quotient of difference in the median frequency between the reference lead and the ST-elevated lead divided by the median frequency of the reference lead.

20. The apparatus in accordance with claim 18, ratio of power in first two peaks to power in the first frequency range or second frequency range is used to characterize the degree of differentiation between STEMI patients and healthy subjects; wherein the ratio in ST-elevated leads is larger than the ratio in reference leads of STEMI patient while the ratios in the two normal leads of healthy subjects are nearly identical.

21. The apparatus in accordance with claim 13, the electrodes include at least one of flexible electrodes, dry electrodes, wet electrodes, and textile electrodes.

\* \* \* \* \*